United States Patent
Ozcan et al.

(10) Patent No.: US 11,893,779 B2
(45) Date of Patent: Feb. 6, 2024

(54) DEVICE AND METHOD FOR MOTILITY-BASED LABEL-FREE DETECTION OF MOTILE OBJECTS IN A FLUID SAMPLE

(71) Applicant: THE REGENTS OF THE UNIVERSITY OF CALIFORNIA, Oakland, CA (US)

(72) Inventors: Aydogan Ozcan, Los Angeles, CA (US); Yibo Zhang, Los Angeles, CA (US); Hatice Ceylan Koydemir, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 363 days.

(21) Appl. No.: 17/285,898

(22) PCT Filed: Oct. 18, 2019

(86) PCT No.: PCT/US2019/057073
§ 371 (c)(1),
(2) Date: Apr. 15, 2021

(87) PCT Pub. No.: WO2020/082030
PCT Pub. Date: Apr. 23, 2020

(65) Prior Publication Data
US 2021/0374381 A1    Dec. 2, 2021

Related U.S. Application Data

(60) Provisional application No. 62/747,285, filed on Oct. 18, 2018.

(51) Int. Cl.
G03H 1/00    (2006.01)
G06T 7/20    (2017.01)
(Continued)

(52) U.S. Cl.
CPC ............. *G06V 10/82* (2022.01); *G01N 15/14* (2013.01); *G01N 33/49* (2013.01);
(Continued)

(58) Field of Classification Search
CPC .................. G01B 11/24; G01N 15/14; G01N 2015/1486; G01N 2021/479;
(Continued)

(56) References Cited

U.S. PATENT DOCUMENTS

| 4,530,304 A | * | 7/1985 | Gardos ..................... B05C 3/05 118/421 |
| 5,483,963 A | * | 1/1996 | Butler ................. G01S 7/52034 600/447 |

(Continued)

OTHER PUBLICATIONS

PCT International Preliminary Report on Patentability (Chapter I of the Patent Cooperation Treaty) for PCT/US2019/057073, Applicant: The Regents of the University of California, Form PCT/IB/326 and 373, dated Apr. 29, 2021 (12 pages).

(Continued)

*Primary Examiner* — Tsung Yin Tsai
(74) *Attorney, Agent, or Firm* — VISTA IP LAW GROUP LLP

(57) ABSTRACT

Systems and methods for detecting motile objects (e.g., parasites) in a fluid sample by utilizing the locomotion of the parasites as a specific biomarker and endogenous contrast mechanism. The imaging platform includes one or more substantially optically transparent sample holders. The imaging platform has a moveable scanning head containing light sources and corresponding image sensor(s) associated with the light source(s). The light source(s) are directed at a respective sample holder containing a sample and the respective image sensor(s) are positioned below a respective sample holder to capture time-varying holographic speckle patterns of the sample contained in the sample holder. The (Continued)

image sensor(s). A computing device is configured to receive time-varying holographic speckle pattern image sequences obtained by the image sensor(s). The computing device generates a 3D contrast map of motile objects within the sample use deep learning-based classifier software to identify the motile objects.

21 Claims, 20 Drawing Sheets

(51) Int. Cl.
　　*G06V 20/69*　　　(2022.01)
　　*G06V 30/19*　　　(2022.01)
　　*G06V 10/82*　　　(2022.01)
　　*G01N 15/14*　　　(2006.01)
　　*G01N 33/49*　　　(2006.01)
　　*G03H 1/08*　　　 (2006.01)
(52) U.S. Cl.
　　CPC .............. *G03H 1/0005* (2013.01); *G03H 1/08* (2013.01); *G06T 7/20* (2013.01); *G06V 20/69* (2022.01); *G06V 20/698* (2022.01); *G06V 30/19173* (2022.01); *G01N 2015/1486* (2013.01); *G03H 2001/0033* (2013.01); *G03H 2210/42* (2013.01); *G03H 2210/46* (2013.01); *G06T 2207/20081* (2013.01); *G06T 2207/30024* (2013.01); *G06T 2207/30242* (2013.01)
(58) Field of Classification Search
　　CPC .... G01N 21/453; G01N 33/487; G01N 33/49; G03H 1/0005; G03H 1/04; G03H 1/08; G03H 2001/0033; G03H 2210/42; G03H 2210/46; G06T 2207/20081; G06T 2207/30024; G06T 2207/30242; G06T 7/20; G06V 10/82; G06V 20/59; G06V 20/968; G06V 30/19173
　　See application file for complete search history.

(56) References Cited

U.S. PATENT DOCUMENTS

| | | | |
|---|---|---|---|
| 5,526,145 A * | 6/1996 | Weber | G02B 5/203 430/1 |
| 5,704,355 A * | 1/1998 | Bridges | A61B 5/0507 600/407 |
| 8,842,901 B2 * | 9/2014 | Ozcan | G01N 15/1463 382/133 |
| 8,886,295 B2 * | 11/2014 | Nolte | H01L 27/146 356/450 |
| 9,222,935 B1 | 12/2015 | Bransky et al. | |
| 9,779,213 B2 * | 10/2017 | Donovan | G16H 50/50 |
| 2009/0206234 A1 | 8/2009 | Okuda | |
| 2010/0184093 A1 * | 7/2010 | Donovan | G16H 50/50 435/287.1 |
| 2010/0331672 A1 * | 12/2010 | Nolte | G01B 9/02032 600/425 |
| 2012/0099803 A1 | 4/2012 | Ozcan | |
| 2012/0148141 A1 * | 6/2012 | Ozcan | G01N 15/1434 382/133 |
| 2012/0157160 A1 | 6/2012 | Ozcan | |
| 2012/0218379 A1 | 8/2012 | Ozcan | |
| 2012/0248292 A1 | 10/2012 | Ozcan | |
| 2012/0258099 A1 * | 10/2012 | Debant | A61K 9/0019 435/235.1 |
| 2012/0281899 A1 | 11/2012 | Ozcan | |
| 2013/0092821 A1 | 4/2013 | Ozcan | |
| 2013/0157351 A1 | 6/2013 | Ozcan | |
| 2013/0193544 A1 | 8/2013 | Ozcan | |
| 2013/0203043 A1 | 8/2013 | Ozcan | |
| 2013/0258091 A1 | 10/2013 | Ozcan | |
| 2013/0260372 A1 | 10/2013 | Buermann et al. | |
| 2013/0280752 A1 | 10/2013 | Ozcan | |
| 2014/0036272 A1 * | 2/2014 | Nadkarni | G01N 21/4795 356/450 |
| 2014/0120563 A1 | 5/2014 | Ozcan | |
| 2014/0160236 A1 | 6/2014 | Ozcan | |
| 2014/0300696 A1 | 10/2014 | Ozcan | |
| 2015/0111201 A1 | 4/2015 | Ozcan | |
| 2015/0153558 A1 | 6/2015 | Ozcan | |
| 2015/0204773 A1 | 7/2015 | Ozcan et al. | |
| 2016/0070092 A1 | 3/2016 | Ozcan | |
| 2016/0161409 A1 | 6/2016 | Ozcan | |
| 2016/0327473 A1 | 11/2016 | Ozcan | |
| 2016/0334614 A1 | 11/2016 | Ozcan | |
| 2016/0346780 A1 | 12/2016 | Bransky et al. | |
| 2017/0160197 A1 | 1/2017 | Ozcan | |
| 2017/0153106 A1 | 6/2017 | Ozcan | |
| 2017/0161545 A1 | 6/2017 | Champlin et al. | |
| 2017/0168285 A1 | 6/2017 | Ozcan | |
| 2017/0220000 A1 | 8/2017 | Ozcan et al. | |
| 2017/0248518 A1 * | 8/2017 | Nadkarni | G01N 33/4833 |
| 2017/0357083 A1 | 12/2017 | Ozcan | |
| 2018/0003686 A1 | 1/2018 | Ozcan | |
| 2018/0052425 A1 | 2/2018 | Ozcan | |
| 2018/0196193 A1 | 7/2018 | Ozcan | |
| 2018/0373921 A1 | 12/2018 | Di Carlo | |
| 2019/0049354 A1 * | 2/2019 | Nadkarni | G01N 21/4738 |
| 2019/0119737 A1 | 4/2019 | Di Carlo | |
| 2019/0137932 A1 | 5/2019 | Ozcan | |
| 2019/0197294 A1 * | 6/2019 | Demirci | G01N 15/1475 |
| 2019/0286053 A1 | 9/2019 | Ozcan | |
| 2019/0294108 A1 | 9/2019 | Ozcan | |
| 2019/0316172 A1 | 10/2019 | Ozcan | |
| 2019/0333199 A1 | 10/2019 | Ozcan | |
| 2019/0346369 A1 | 11/2019 | Ozcan | |
| 2020/0103328 A1 | 4/2020 | Ozcan | |
| 2020/0310100 A1 | 10/2020 | Ozcan | |
| 2020/0340901 A1 | 10/2020 | Ozcan | |
| 2020/0393359 A1 | 12/2020 | Ozcan | |
| 2020/0393793 A1 | 12/2020 | Ozcan | |
| 2021/0043331 A1 | 2/2021 | Ozcan | |

OTHER PUBLICATIONS

Response to Extended European Search Report under Rules 70(2) and 70a(2) EPC dated Jul. 13, 2022, for European Patent Application No. 19872362.0-1001, Applicant: The Regents of the University of California, (95 pages).
The extended European search report dated Dec. 7, 2021 for European Patent Application No. 19872362.0-1001, Applicant: The Regents of the University of California, (12 pages).
Communication pursuant to Rules 70(2) and 70a(2) EPC dated Jan. 3, 2022, for European Patent Application No. 19872362.0-1001, Applicant: The Regents of the University of California, (1 page).
Jay M. Newby et al., Convolutional neural networks automate detection for tracking of submicron scale particles in 2D and 3D, Arxiv.org, Cornell University Library, 201 Olin Library Cornell University Ithaca, NY 14853, Apr. 10, 2017, XP081418971, DOI:10.1073/PNAS.1804420115 (18 pages).
Sylvie Bisser et al., Sensitivity and Specificity of a Prototype Rapid Diagnostic Test for the Detection of Trypanosoma brucei gambiense Infection: A Multi-centric Prospective Study, PLOS Neglected Tropical Diseases, DOI:10.1371, journal.pntd.0004608, Apr. 8, 2016 (16 pages).
Mustafa Ugur Daloglu et al., Computational imaging of sperm locomotion, Biology of Reproduction, 2017, 97(2), 182-188, doi:10.1093/biolre/iox086.
Michael V. D'Ambrosio, et al., Point-of-care quantification of blood-borne filarial parasites with a mobile phone microscope, www.ScienceTranslationalMedicine.org, May 6, 2015, vol. 7, Issue 286 286re4.
Xavier Glorot et al., Understanding the difficulty of training deep feedforward neural networks, Journal of Machine Learning Research, Jan. 2010, https://www.researchgate.net/publication/215616968.

(56) References Cited

OTHER PUBLICATIONS

Niko Heddergott et al., Trypanosome Motion Represents an Adaptation to the Crowded Environment of the Vertebrate Bloodstream, (2012), PLoS Pathog 8(11): e1003023. doi:10.1371/journal.ppat. 1003023.

Diederik P. Kingma et al., ADAM: a Method for Stochastic Optimization, Published as a conference paper at ICLR 2015.

P. Memmolo et al., Automatic focusing in digital holography and its application to stretched holograms, May 15, 2011, vol. 36, No. 10, Optics Letters, 1945-1947.

Bob Storey et al., Utilization of computer processed high definition video imaging for measuring motility of microscopic nematode stages on a quantitative scale: "The Worminator", International Journal for Parasitology: Drugs and Drug Resistance—Aug. 2014, https://www.researchgate.net/publication/265170695.

Ting-Wei Su et al., Compact and Light-Weight Automated Semen Analysis Platform Using Lensfree on-Chip Microscopy, Anal. Chem. 2010, 82, 8307-8312.

Ting-Wei Su et al., High-throughput lensfree 3D tracking of human sperms reveals rare statistics of helical trajectories. www.pnas.org/cgi/doi/10.1073/pnas.1212506109, PNAS, 16018-16022, vol. 109, No. 40, Oct. 2, 2012.

Miu Tamamitsu et al., Comparison of Gini index and Tamura coefficient for holographic autofocusing based on the edge sparsity of the complex optical wavefront.

Yibo Zhang et al., Edge sparsity criterion for robust holographic autofocusing, Optics Letters, vol. 42, No. 19, Oct. 1, 2017, 3824-3827, https://www.researchgate.net/publication/319988933.

PCT International Search Report and Written Opinion for PCT/US2019/057073 dated Jan. 6, 2020, Applicant: The Regents of the University of California (13 pages).

Notification of the First Office Action dated Jul. 28, 2023 for Chinese Patent Appl No. 2019800793540, Applicant: The Regents of the University of California, (29 pages).

\* cited by examiner

Step (a)
Raw frames acquired by each image sensor

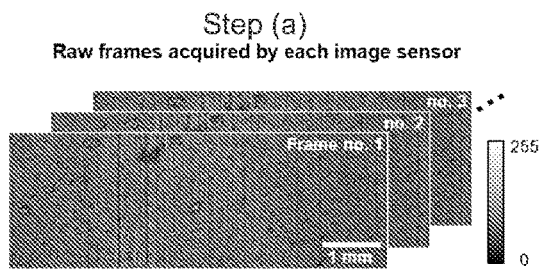

FIG. 3A

Step (b)
Correction of illumination non-uniformity and normalization by mean value

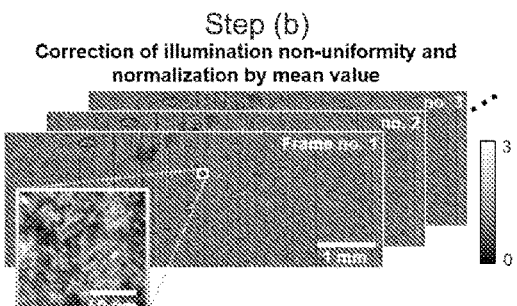

FIG. 3B

Step (c)
Autofocusing to locate the bottom of the fluid sample

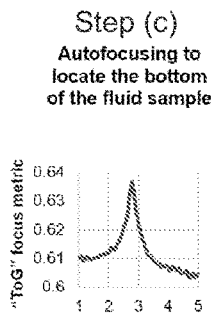

FIG. 3C

Step (d)
High-pass filtered back-propagation

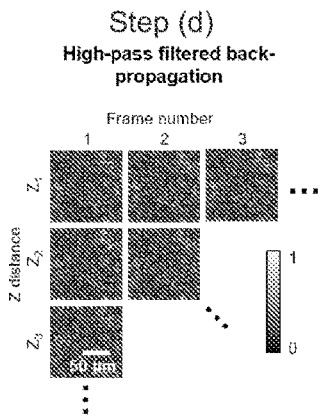

FIG. 3D

Step (e)
Differential analysis with object function normalization

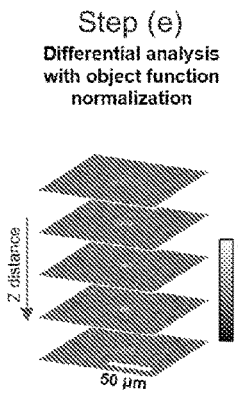

FIG. 3E

Step (f)
High-pass filtering in Z

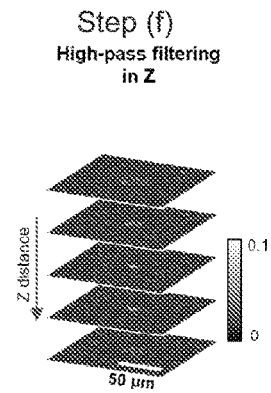

FIG. 3F

Step (g)
Maximum intensity projection along Z

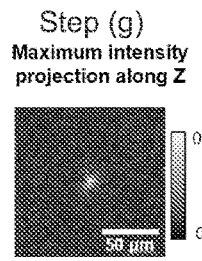

FIG. 3G

Step (h)
High-pass filtering in XY

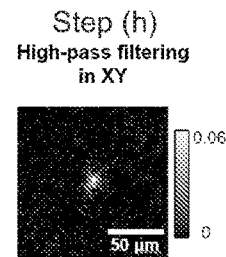

FIG. 3H

Step (i)
Threshold and find connected regions

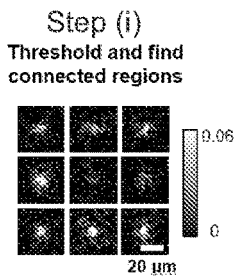

FIG. 3I

Step (j)
Deep learning-based classification

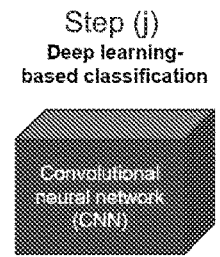

FIG. 3J

Step (k)
Generate test result

| Screen whole blood volume (mL) | 0.79 |
| Detected no. of parasites | 5 |
| Parasite concentration (mL⁻¹) | 6.3 |

FIG. 3K

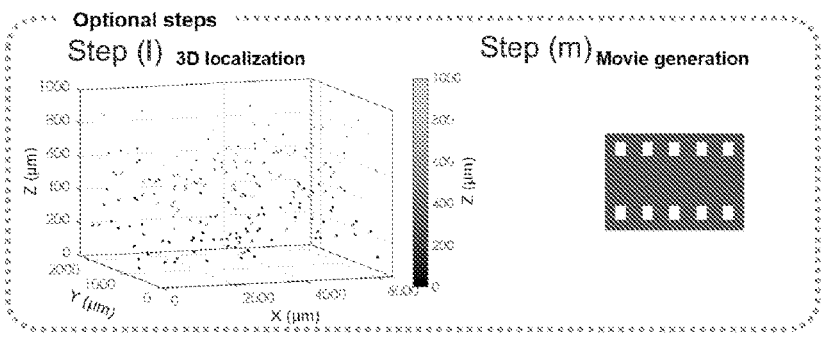

Optional steps
Step (l) 3D localization

FIG. 3L

Step (m) Movie generation

FIG. 3M

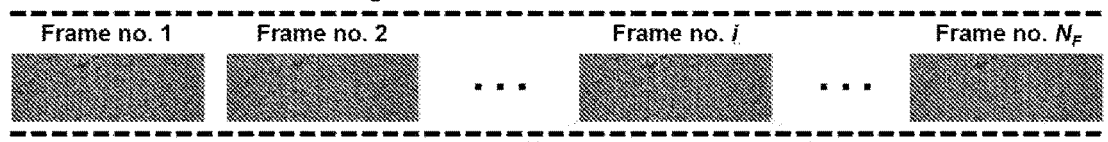
*FIG. 4A*
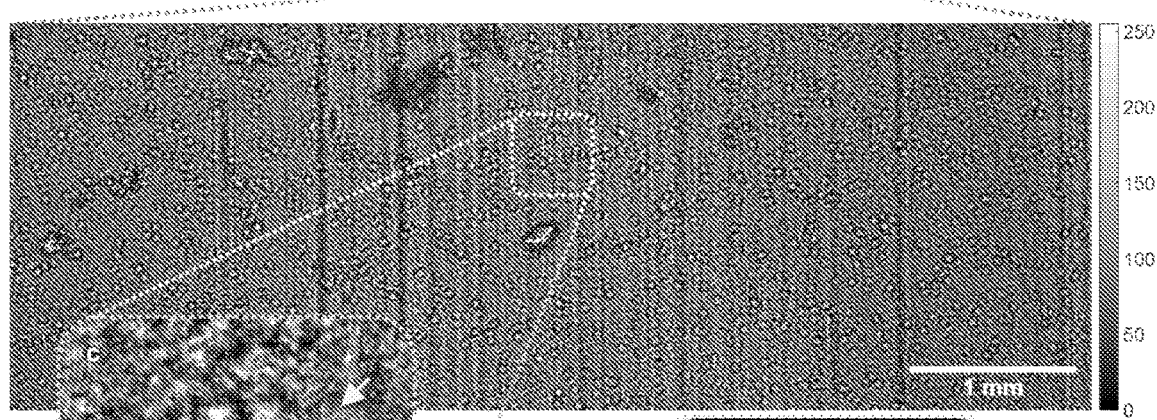
*FIG. 4B*
*FIG. 4C*
*FIG. 4E*
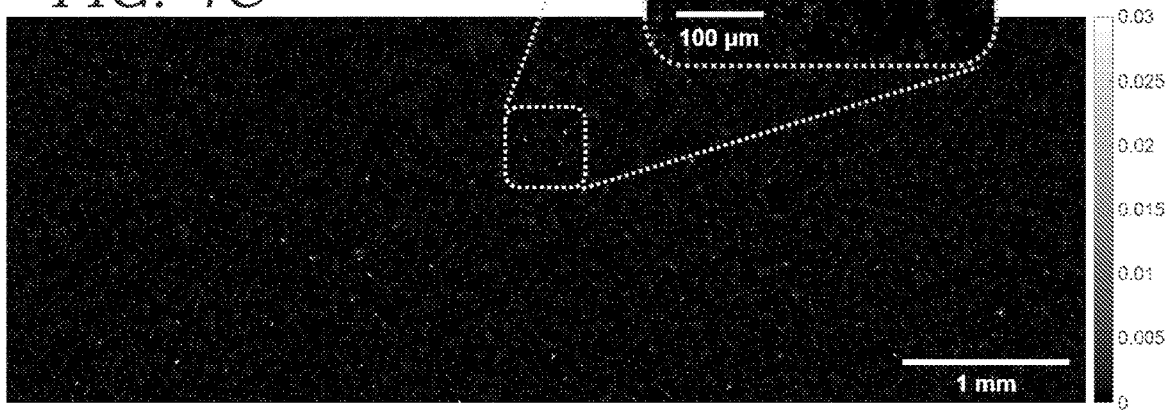
*FIG. 4D*

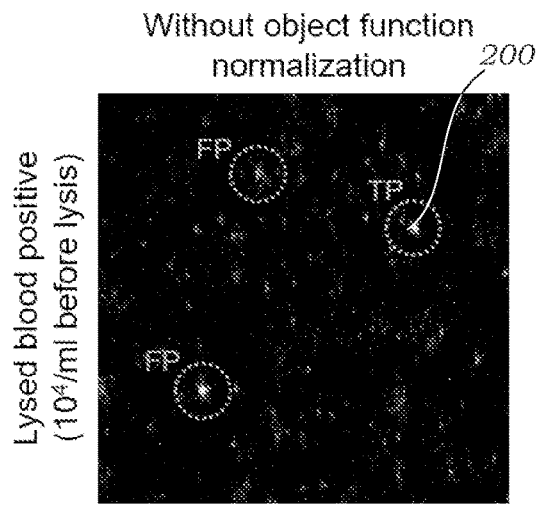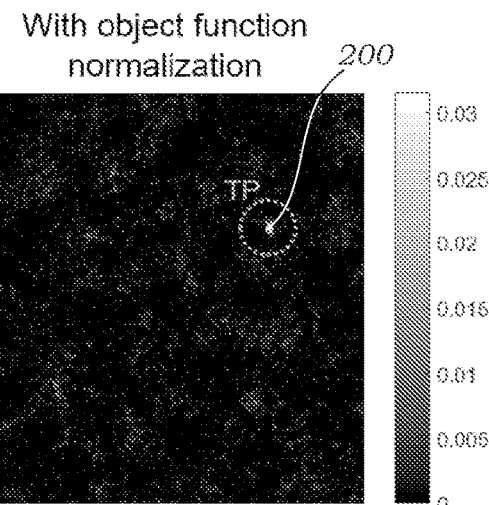
FIG. 11A   FIG. 11B
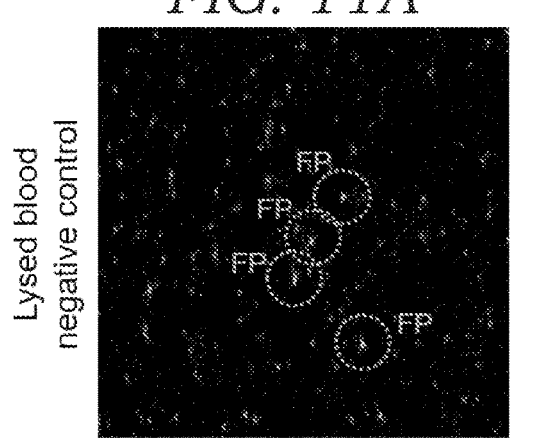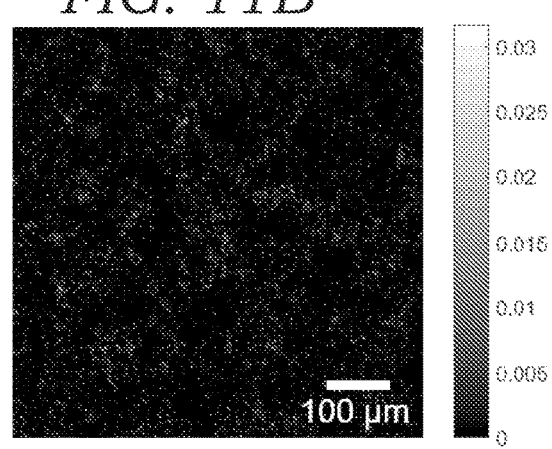
FIG. 11C   FIG. 11D
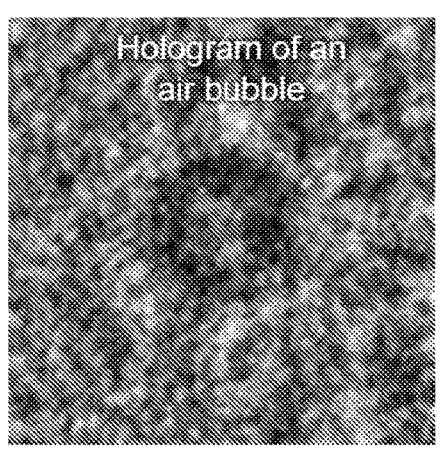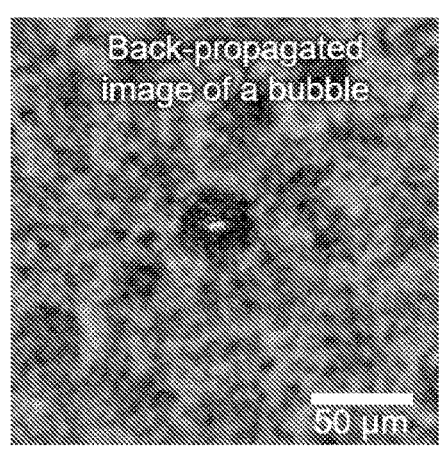
FIG. 11E   FIG. 11F

| | Parasite Stage | | | | | | | LoD/Sensitivity/Specificity | Blood volume analyzed | CSF volume analyzed | Expert requirement (e.g., benchtop microscope) | Benchtop device requirement for sample preparation (e.g., centrifugation) | Electricity requirement | Field-portable | Microscopic examination of parasites manually | Total analysis time per test |
| | T. cruzi | | T. brucei gambiense | | T. brucei gambiense | | Blood | CSF | | | | | | | | | |
| | Acute | Chronic | I | II | I | II | | | | | | | | | | | |
|---|---|---|---|---|---|---|---|---|---|---|---|---|---|---|---|---|---|
| mAECT tubes [i] | | | ✓ | ✓ | | ✓ | ✓ | ✓ | <50 trypanosomes / mL | 350 μL / test | | Yes | Yes | Yes | No | Yes | 45-60 min |
| PCR | ✓ | ✓ | ✓ | ✓ | ✓ | ✓ | ✓ | ✓ | High sensitivity and specificity for T. brucei gambiense and T. cruzi [36] Low sensitivity for T. brucei rhodesiense [35] | 200 μL | 1000 μL | Yes | Yes | Yes | No | Yes | ~5 h [ii] |
| Thick smear | ✓ | | ✓ | ✓ | ✓ | ✓ | ✓ | ✓ | Low sensitivity | 2-4 μL / slide | 2-4 μL / slide | Yes | Yes | Yes | Yes | No | 75-90 min |
| Microhaematocrit | ✓ | | ✓ | ✓ | ✓ | ✓ | ✓ | ✓ | High sensitivity for T.b. gambiense and T.b. rhodesiense (an estimated detection threshold of 500 trypanosomes/ml) [18] | 6 × 50-75 μL / tube | | Yes | Yes | Yes | No | Yes | ~15 min |
| Strout method | ✓ | | | | | | ✓ | | Low sensitivity | 2-4 μL/slide [iii] | | Yes | Yes | Yes | No | Yes | ~30 min [iv] |
| Card agglutination test for trypanosomiasis (CATT) | | | ✓ | ✓ | | | ✓ | | High specificity and sensitivity for T.b. gambiense [v] Not for T.b. cruzi and T.b. rhodesiense | 30-50 | | No | No | No [vi] | Yes | No | 5 min |
| Rapid diagnostic tests | ✓ | ✓ | ✓ | ✓ | | | ✓ | | Low specificity, especially for low parasitemia levels [4] | 30 μL | | No | No | No | Yes | No | 15 min |
| Our method | ✓ | ✓ | ✓ | ✓ | ✓ | ✓ | ✓ | ✓ | 10 trypanosomes / mL for blood 3 trypanosomes / mL for CSF | ~800 μL | ~3200 μL | No | No | Yes | Yes | - | ~20 min |

*FIG. 14*

[i] This method can be made even more sensitive (10 trypanosomes/mL) by doing centrifugation of whole blood and loading buffy coat onto the mAECT tube
[ii] including DNA isolation, PCR, and electrophoresis.
[iii] The blood analyzed (2-4 uL) is taken from a centrifuged/concentrated blood sample.
[iv] 5 min for centrifugation plus time required to analyze each slide.

DEVICE AND METHOD FOR MOTILITY-BASED LABEL-FREE DETECTION OF MOTILE OBJECTS IN A FLUID SAMPLE

RELATED APPLICATION

This Application is a U.S. National Stage filing under 35 U.S.C. § 371 of International Application No. PCT/US2019/057073, filed Oct. 18, 2019, which claims priority to U.S. Provisional Patent Application No. 62/747,285 filed on Oct. 18, 2018, and is hereby incorporated by reference in its entirety. Priority is claimed pursuant to 35 U.S.C. §§ 119, 371 and any other applicable statute(s).

TECHNICAL FIELD

The technical field generally relates to devices and methods used to detect moving objects in bodily fluids. One particular embodiment involves detecting and counting parasites in bodily fluids. The devices and methods utilize holographic speckle analysis and deep learning to detect moving objects such as parasites in bodily fluids.

BACKGROUND

Parasitic infections affect billions of people globally, resulting in massive socioeconomic burden. Although usually associated with low-income countries, parasitic infections are also becoming an increasing health concern in developed countries. In the United States alone, millions of people are affected by various parasites, which can lead to severe illnesses and even death. Motility is common among disease-causing organisms, from unicellular pathogenic bacteria and parasitic protozoa to multicellular parasitic worms and ectoparasites. Motility is the ability of a cell or organism to move of its own accord using its own energy. The ability of an organism to move itself from one location to another has obvious benefits for successful infection and transmission, and motility is often central to virulence. Despite the importance of motility for a parasitic lifestyle, parasite motility remains an understudied area of research and motility-based diagnostics are largely underexplored.

Human African trypanosomiasis (HAT), also known as sleeping sickness, and Chagas disease (i.e., American trypanosomiasis) are examples of neglected tropical diseases (NTDs) caused by motile protozoan parasites. As NTDs, they have historically been given little attention, disproportionately affect the world's poorest people, and lack adequate medical interventions for diagnosis and treatment. There are no vaccines, and existing chemotherapeutics suffer from high toxicity and drug resistance. These two devastating diseases, HAT and Chagas disease, are caused by related trypanosome parasites. *Trypanosoma brucei* (*T. brucei gambiense* and *T. brucei rhodesiense* subspecies) is responsible for HAT, and related species cause animal diseases that present a substantial economic burden in some of the poorest areas of the world. The parasite is transmitted to humans by the tsetse fly and survives extracellularly in blood and tissues, with dramatic impacts on the central nervous system (CNS). HAT is endemic in ~30 sub-Saharan Africa countries with ~65 million people at risk of infection. The number of reported cases has dropped to historic lows, but past declines in case numbers have been followed by major epidemics. Therefore, HAT remains an important human health risk. Chagas disease, on the other hand, is caused by *Trypanosoma cruzi* (*T. cruzi*), which invades and replicates inside host cells causing severe pathology within host tissues. Chagas disease is mostly transmitted by the bite of triatomine bugs, but other transmission routes include blood transfusion and ingestion of contaminated food or drink. The disease is endemic in Latin America where it affects over 6 million people. It is estimated that more than 300,000 people are infected in the United States with further increases expected as globalization and climate change impact the distribution of disease-transmitting vectors.

Both trypanosomiases can be classified into an initial stage during which trypanosomes circulate in the bloodstream and medical treatment is most effective (stage I HAT and acute Chagas disease), and a later stage that is exceedingly more difficult, if not impossible, to cure (stage II HAT and chronic Chagas disease). Therefore, early detection is crucial for both diseases. However, rapid and sensitive diagnosis remains challenging, particularly in resource-limited settings. In the diagnosis of HAT, it is also essential to assess the stage of the disease to determine the appropriate therapeutic strategy. While trypanosomes remain in the blood and lymph in stage I HAT, stage II HAT is characterized by trypanosomes crossing the blood-brain barrier and invading the central nervous system (CNS), causing neurological symptoms and eventually death if untreated. Because the drugs used to treat stage I and stage II HAT are not interchangeable, and drugs for stage II may be more toxic, it is very important to identify the stage of the disease to inform the selection of treatment regimen. Stage determination is currently done by collecting cerebrospinal fluid (CSF) via a lumbar puncture and examining the CSF under a microscope for presence of white blood cells (WBCs) and trypanosomes.

Both trypanosome species are typically ~20 µm in length and ~3 µm in width and use flagellum-mediated motility for parasite propulsion. The detection of these motile parasites in large volume bodily fluids such as blood and CSF are an important clinical challenge. For decades, the standard screening test for *T. b. gambiense* HAT has been the card agglutination test for trypanosomiasis (CATT), which detects the presence of antibodies against a specific parasite antigen. However, CATT suffers from practical limitations as well as low specificity and sensitivity in some areas. Moreover, a positive CATT test must typically be confirmed with direct visual observation in blood samples. Several molecular and immunological detection methods have been developed including polymerase chain reaction (PCR) and rapid diagnostic tests (RDTs), but these methods are limited by insufficient specificity or sensitivity, the need for sophisticated equipment and highly trained personnel, or high production costs. Thus, microscopic evaluation is still widely used for primary or secondary diagnosis, and direct observation of CSF remains the sole method for HAT stage determination. Each milliliter of whole blood typically contains billions of red blood cells (RBCs), millions of white blood cells (WBCs) and hundreds of millions of platelets. In contrast, blood parasitemia fluctuates during the course of infection and often is below 100 parasites/mL, making microscopic identification of trypanosomes a needle-in-a-haystack problem. The low sensitivity of direct observation methods therefore requires analytical separation devices such as centrifugation or ion exchange purification, which partially limit analysis in resource-limited settings. Thus, there is still a major need for development of new methods with high sensitivity and throughput that can reduce costs and simplify diagnosis.

SUMMARY

To address this important challenge, the present invention is directed to systems and methods for detecting motile objects in a sample, which may be used, for example, in detecting parasites in bodily fluids. The systems and methods utilize a cost-effective and field-portable optical device based on lensless, time-resolved holographic speckle imaging, for label-free, high-throughput and sensitive detection of motile parasites in various bodily fluids and turbid media. Instead of staining a target analyte or using molecular biomarkers, the technique utilizes the locomotion of self-propelling parasites (or other motile microorganisms or cells) as a biomarker and endogenous contrast mechanism. As a result, the sample preparation is very simple and fast, does not require any benchtop-scale sample processing device/equipment and does not require refrigeration, centrifugation or purification.

Accordingly, one embodiment of the present invention is directed to an imaging platform for label-free detection of motile objects in a sample. For instance, the motile objects may be organisms such as parasites or other suitable motile objects. The imaging platform includes one or more substantially optically transparent sample holders, such as capillary tubes or other suitable sample holders. The imaging platform also has a moveable scanning head containing one or more coherent light sources and corresponding image sensor(s) associated with the one or more coherent light sources. For example, the scanning head may only a single coherent light source (e.g., a laser diode) and a single image sensor (e.g., a complementary metal-oxide-semiconductor (CMOS)), or the scanning head may have a coherent light source and an image sensor for each sample holder. The coherent light source(s) are directed at a respective sample holder and the respective image sensor(s) are positioned below a respective sample holder to obtain image sequences of a sample contained in the sample holder. As an example, the image sensor(s) may record time-varying holographic speckle patterns (e.g., "movies") of the sample contained in the sample holder.

The imaging platform has a computing device configured to receive time-varying holographic speckle pattern image sequences obtained by the image sensor(s). The computing device includes computational motion analysis software configured to generate a three-dimensional (3D) contrast map of motile objects within the one or more sample holders. The computing device also has deep learning-based classifier software to identify motile objects in the three-dimensional (3D) contrast map.

In another aspect, the imaging platform may also include a translation stage configured to translate the moveable scanning head along the one or more sample holders. For example, the translation stage may be configured to move the scanning head linearly along the one or more optically transparent sample holder to allow the scanning head to obtain image sequences at different sections of the sample holder(s), for example, different sections along the length of the sample holder(s).

In another aspect of the imaging platform, the sample comprises a biological fluid, such as blood. In still another aspect, the biological fluid comprises blood or cerebrospinal fluid.

In yet another aspect, the sample holders are one or more capillary tubes. For instance, the capillary tubes may be elongated rectangular tubes (i.e., having a rectangular cross-section).

In another aspect of the imaging platform, the one or more coherent light sources may be laser diode(s), light-emitting diode(s), and/or laser(s), or any combination of the foregoing, which project light onto the one or more sample holders.

In still another aspect, the translation stage may include one or more linear motion shafts holding the moveable scanning head and a stepper motor coupled to the moveable scanning head via a belt. The translation stage may be configured to move the scanning head to capture time-varying holographic speckle patterns along different regions or areas of the sample holder(s).

In another feature of the imaging platform, the moveable scanning head may further comprise one or more heat sinks for the image sensor(s). For instance, the heat sinks may be arranged to dissipate heat generated by the circuit board(s) operably coupled to the image sensors. The heat sinks may be customized, metallic (e.g., aluminum) elements, and may be disposed between the circuit board(s) and each image sensor to prevent the image sensors from being damaged or malfunctioning due to overheating.

In another aspect, the computational motion analysis software is configured to perform object function normalization (OFN) to suppress strongly scattering objects within the sample.

Another embodiment of the present invention is directed to a method of using the imaging platform, for example, to detect motile objects in a fluid sample. The method includes loading a fluid sample into the one or more substantially optically transparent sample holders. The moveable scanning head is translated to different regions of the one or more sample holders. The image sensor(s) obtain time-varying holographic speckle pattern image sequences of the fluid sample. Then, the computing device identifies one or more motile objects in the sample using the deep learning-based classifier software.

In another aspect of the method, the computing device identifies on or more motile objects in the image sequences by generating a three-dimensional (3D) contrast map of motile objects in the image sequences using the computational motion analysis software, and then identifying the motile objects in the three-dimensional (3D) contrast map of motile objects using the deep learning-based classifier software.

In another aspect of the method of using the imaging platform, prior to loading the fluid sample into the sample holders, the fluid sample is first exposed to a lysis buffer.

In still another aspect of the method, the fluid sample is allowed to settle prior to translating the moveable scanning head and the image sensor(s) obtaining time-varying holographic speckle pattern image sequences of the fluid sample.

In yet another aspect of the method, the deep learning-based classifier software determines and/or outputs a count of motile objects in the sample. In still another aspect, the deep learning-based classifier software determines and/or outputs a concentration of motile objects in the sample.

In another aspect of the method, the deep learning-based classifier software outputs a positive or negative classification for the sample. This may be separate from or in addition to obtaining counts and/or concentrations of motile objects in the sample For instance, the deep learning-based classifier software may be used to count the number of motile species in the sample which can then be used to calculate the concentration of the motile objects in the sample (given a known volume of sample), and then classify a particular sample as positive (+) or negative (−) for a target motile object based on the count or concentration of motile objects. For example, threshold cutoff values may be used to demarcate between a positive or negative sample.

In another aspect of the method, the sample comprises a biological sample. In still another aspect, the sample comprises an environmental sample. In another aspect, the motile objects comprise parasites.

Another embodiment of the present invention is directed to a method of detecting motile objects in a sample. The method includes obtaining a plurality of time-varying holographic speckle pattern image sequences of the sample using a moveable scanning head containing one or more coherent light sources and corresponding image sensor(s) associated with the one or more coherent light sources. The plurality of time-varying holographic speckle pattern image sequences are processed with a computing device configured to receive the time-varying holographic speckle pattern image sequences obtained by the image sensor(s). The computing device includes computational motion analysis software configured to generate a three-dimensional (3D) contrast map of motile objects within the one or more sample holders, and a deep learning-based classifier software to identify motile objects in the three-dimensional (3D) contrast map.

In another aspect, the method further includes the computing device generating a three-dimensional (3D) contrast map of motile objects within the one or more sample holders using the computational motion analysis software. Then, the computing device identifies motile objects in the three-dimensional (3D) contrast map using the deep learning-based classifier software.

In another aspect, the method also includes the computing device determining and/or outputting a count of the motile objects. In still another aspect, the method includes the computing device determining and/or outputting a concentration of the motile objects in the sample.

In one example of the imaging platform, the fluid sample to be screened is illuminated by a coherent light source (e.g., a laser diode), and a complementary metal-oxide-semiconductor (CMOS) image sensor is placed below the sample to record the time-varying holographic speckle patterns (e.g., "movies") of the sample. The time-varying holographic speckle patterns may be obtained using a scanning head that moves to different regions of a three-dimensional volume that contains the sample to be analyzed. The scanning head may include a plurality of light sources and image sensors that can image multiple samples in parallel (or a single sample divided into multiple test volumes). Of course, in other embodiments, only a single light source and image sensor may be used.

The image sequence obtained by the image sensor(s) is then analyzed by a custom-written computational motion analysis (CMA) algorithm based on holography to generate a three-dimensional (3D) contrast map that is specific to the locomotion of the parasites in the sample volume. Finally, a deep learning-based classifier is used to automatically detect and count the signal patterns of the parasites (or other motile species) using the reconstructed 3D locomotion map (see FIGS. 3A-3M).

An exemplary imaging platform according to the present invention was constructed and configured to increase the throughput and reduce the limit of detection (LoD) for rapid screening of large fluid volumes (~3.2 mL or larger). In this example, the imaging platform includes three identical lensless speckle imaging modules mounted on a translation stage to screen three individual sample tubes in parallel. Each imaging module is translated to different sections of the capillary tube containing the liquid sample, where the CMOS image sensor captures high-frame-rate video sequences before moving on to the next section. Using this approach, ~3.2 mL, or more, of fluid sample may be prepared, screened and analyzed, all within ~20 minutes, using the exemplary imaging platform. Compared to standard benchtop optical microscopes, this imaging platform design provides orders of magnitude increase in the screened sample volume (which is very important for the detection of parasites at low concentrations). In addition, the imaging platform may be significantly more compact and lightweight (e.g., weighing about 1.69 kg or less). Furthermore, since a relatively large sample volume is screened computationally in the axial direction, the imaging device does not need high precision in its opto-mechanical design, which also makes the platform highly cost-effective, where its parts may cost about $1,850 or less in total even under very low volume manufacturing.

The exemplary imaging platform was tested using trypanosomes to test the mobile platform and it demonstrated its capability to detect parasites in spiked whole blood and CSF samples, which are important for the diagnosis and stage determination of HAT as well as the diagnosis of acute Chagas disease. The spiking experiments were performed at a series of concentrations using *T. brucei* (a non-human infectious subspecies of *Trypanosoma*) as a model parasite for *T.b. gambiense, T.b. rhodesiense* and *T. cruzi*. Through deep learning-based classification, it was shown that as low as 10 parasites per mL of whole blood and 3 parasites per mL of CSF can be reliably detected using the imaging platform. Furthermore, the success of the platform to detect other motile parasites in bodily fluids by imaging *Trichomonas vaginalis* (*T. vaginalis*), the protozoan parasite responsible for trichomoniasis, which is the most common, non-viral sexually transmitted disease (STD) affecting 3.7 million people in the United States and 275 million worldwide, was demonstrated. Accordingly, the label-free, motility-based parasite detection platform can provide a cost-effective and portable approach for rapid and sensitive screening of trypanosomes and other motile parasites in resource-limited settings, or as a high-throughput analytical research tool to study motile organisms in 3D. While the exemplary imaging platform described herein was used to detect parasites, it should be understood that the platform may be used in the detection of other motile species that are not parasites. For example, this includes sperm and other multicellular or single cellular species that are motile.

BRIEF DESCRIPTION OF THE DRAWINGS

The foregoing and other aspects of embodiments are described in further detail with reference to the accompanying drawings, wherein like reference numerals refer to like elements and the description for like elements shall be applicable for all described embodiments wherever relevant. Reference numerals having the same reference number and different letters (e.g., 104a, 104b, 104c) refer to like elements and the use of the number without the letter in the Detailed Description refers to each of the like elements.

FIGS. 3A-3M illustrate a CMA algorithm with OFN, combined with deep learning-based identification, for sensitive and label-free detection of trypanosomes in lysed blood, according to one embodiment of the present invention. The steps are performed in the same order as listed (steps a-k) with optional steps (l) and (m).

FIGS. 4A-4E are images illustrating the results of an experimental demonstration of applying the CMA algorithm and OFN to a lysed blood sample spiked with motile trypanosome parasites, over a field of view (FOV) of ~14.7 mm$^2$, according to one embodiment of the present invention. FIG. 4A is a time-sequence of the diffraction or speckle patterns of the sample captured by an image sensor or an imaging platform as shown in FIG. 1A, according to one embodiment of the present invention. FIGS. 4A-4C show the raw speckle patterns of a lysed, trypanosome-spiked whole blood sample captured by the image sensor. FIGS. 4B and 4C show a magnified view of one of the frames in the raw image sequence. FIGS. 4D and 4E show the motile parasites detected after being processed by a CMA algorithm, according to one embodiment of the present invention. FIG. 4E shows an example of calculated 3D location of hotspots which can be used to create in-focus movies of amplitude and phase channels of back-propagated diffraction patterns, according to one embodiment of the present invention.

FIG. 5A is a calibration curve for trypanosome detection in lysed whole blood (logarithmic scale). The dashed line indicates expected values (y=x). Measured values are indicated by the dots showing data points. The error bars show the standard deviation of 3 independent measurements indicated by the dots showing data points. FIG. 5B is a zoomed-in view of FIG. 5A showing the low concentration measurements (linear scale), including the negative control (no trypanosomes). No false positives were found in the three negative control samples. FIGS. 5C and 5D are calibration curves for trypanosome detection in artificial CSF, similar to FIGS. 5A and 5B. The dashed line in FIG. 5D corresponds to the mean±3×SD of the negative control result.

FIG. 6A is one of the raw holograms in the image sequence. FIG. 6B is an example of an image that is processed by the CMA algorithm with OFN. FIG. 6B shows five signal spots.

FIG. 7A is one of the raw holograms in the image sequence. FIG. 7B is an example of an image that is processed by the CMA algorithm. Because *trichomonas* has a strong optical phase, OFN is not applied here. FIG. 7B shows three signal spots.

FIG. 8A is one of the raw holograms in the image sequence. FIG. 8B is an example of an image that is processed by the CMA algorithm without OFN. FIG. 8B shows three signal spots.

FIGS. 9A and 9B show the optimization for trypanosome detection in lysed blood, in which $\delta_F=4$ and $N_F=61$, leading to the optimal SNR of 35.29 dB. FIGS. 9C and 9D show the optimization for trypanosome detection in CSF, in which $\delta_F=4$ and $N_F=41$, leading to the optimal SNR of 45.00 dB.

FIG. 10A is graphic illustrating the velocity magnitude distribution after a 1 mm-height glass tube is heated for 7 seconds (side view). The middle cross section of the glass tube is shown. FIG. 10B is a graph showing the maximum fluid velocity magnitude within the glass tube, as a function of time being heated. Different curves correspond to different inner heights of the glass tube. FIG. 10C is a graph showing the maximum fluid velocity magnitude after being heated for 7 seconds as a function of the channel height.

FIGS. 11A-11F are images illustrating how OFN suppresses potential "false positives" due to strongly scattering particles, demonstrated in lysed blood. TP indicates "true positive" spots corresponding to trypanosomes; FP indicates "false positives." The false positives in the negative control sample FIG. 11C are suppressed after applying OFN as shown in FIG. 11D, whereas the true positive signal is preserved ("TP" in FIGS. 11A and 11B). In the positive sample, a strong false positive is created due to an air bubble ("FP" in the bottom left of FIG. 11A), whose hologram and back-propagated amplitude image are shown in FIGS. 11E and 11F, respectively. As shown in FIG. 11B, the strong false positive is effectively eliminated by OFN.

FIG. 14 is a table that compares various existing detection methods with the currently disclosed method.

DETAILED DESCRIPTION OF ILLUSTRATED EMBODIMENTS

Figure 1A:
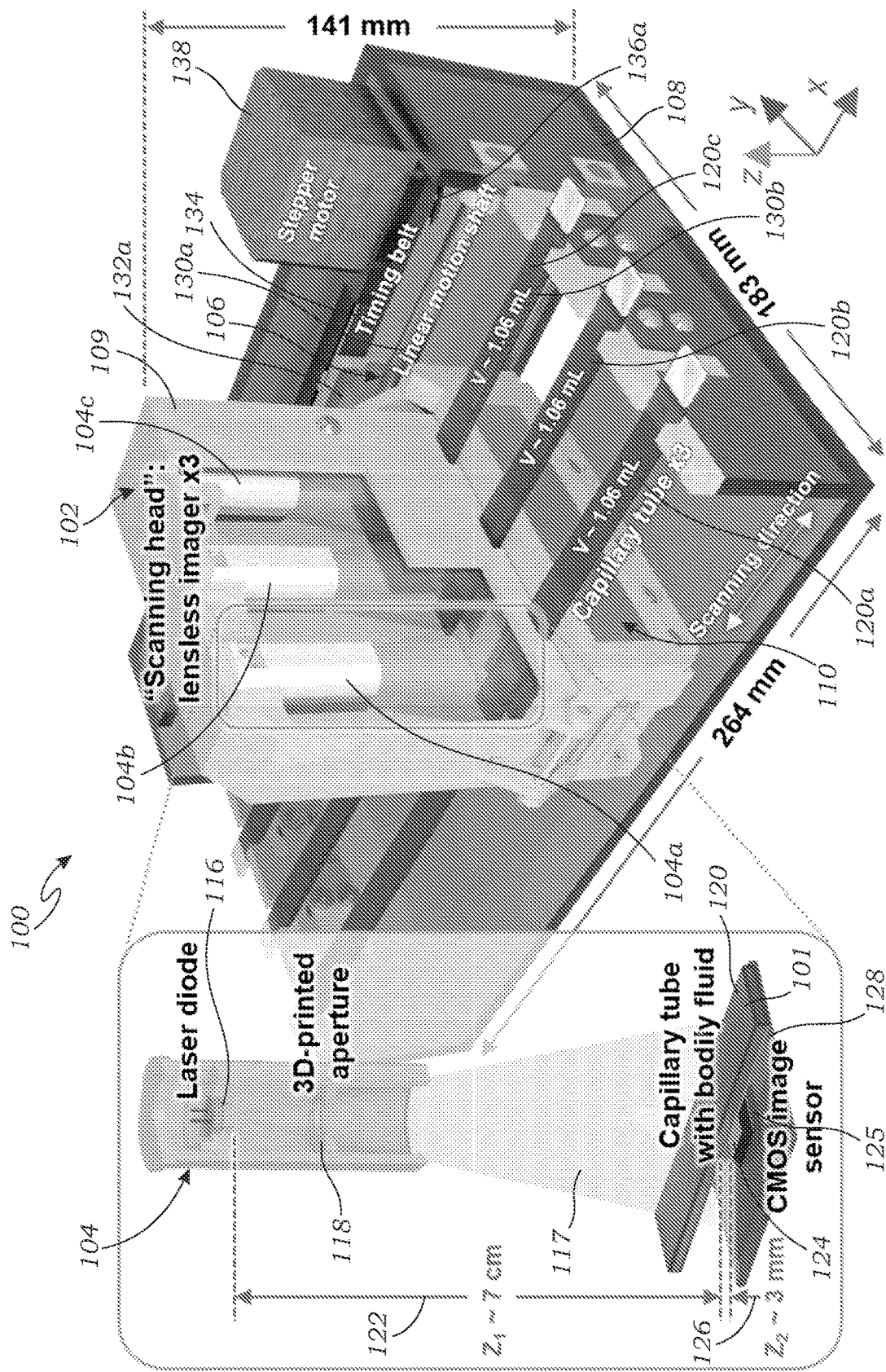
FIG. 1A is a schematic illustration of an imaging platform for detecting motile objects in a sample, according to one embodiment of the present invention. The device is based on lensless holographic time-resolved speckle imaging. The dimensions are for illustration purposes only and may vary beyond those specifically illustrated in FIG. 1A. The device illustrated is a high-throughput bodily fluid screening device which screens and analyzes ~3.2 mL of fluid sample within ~20 minutes.
Figure 1B:
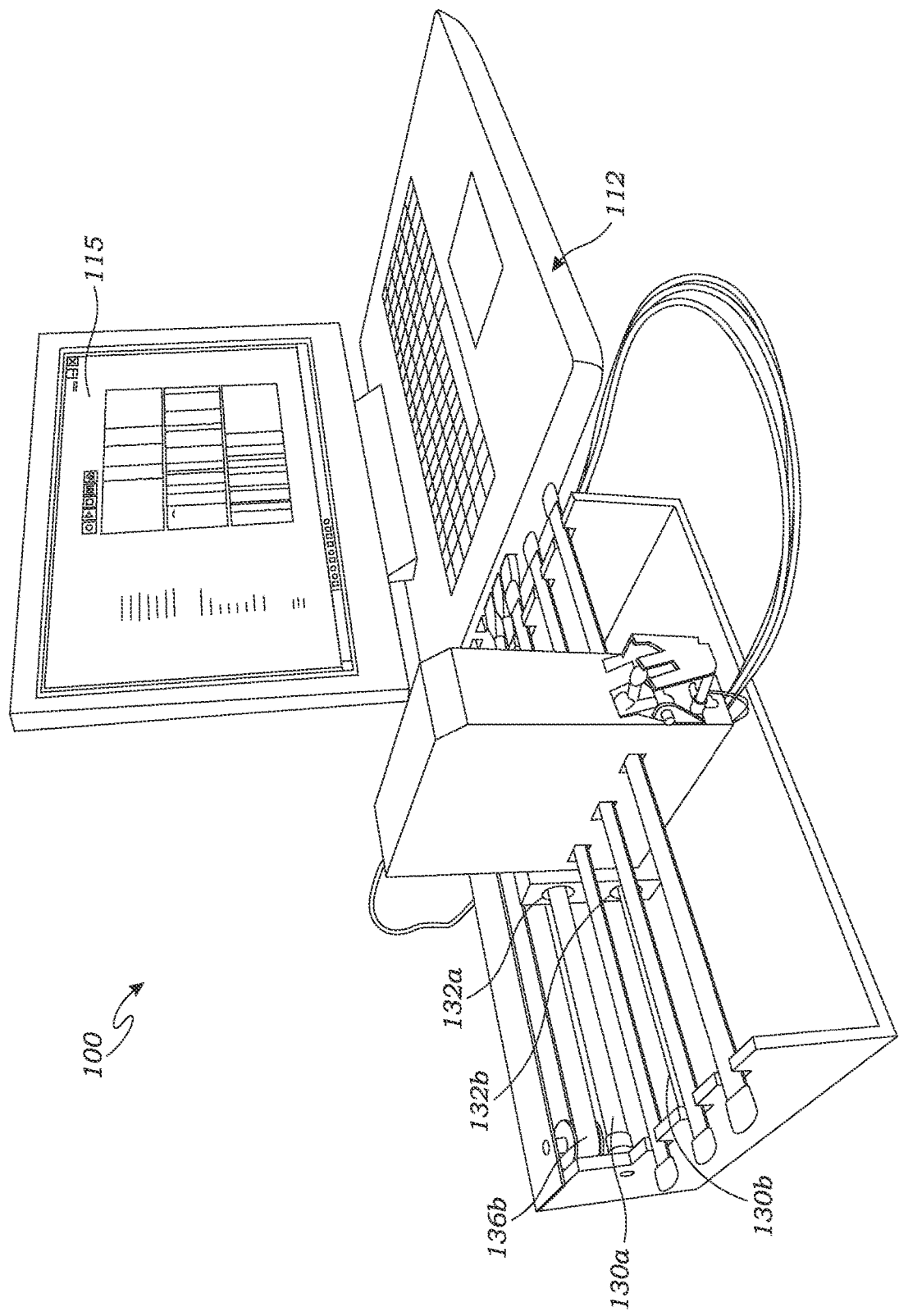
FIG. 1B is a photograph of an exemplary embodiment of an imaging platform fabricated according to the schematic illustration of FIG. 1A. The imaging platform of FIG. 1B is controlled by a computing device (e.g., laptop), which is also used for processing of the acquired data.
Figure 1C:
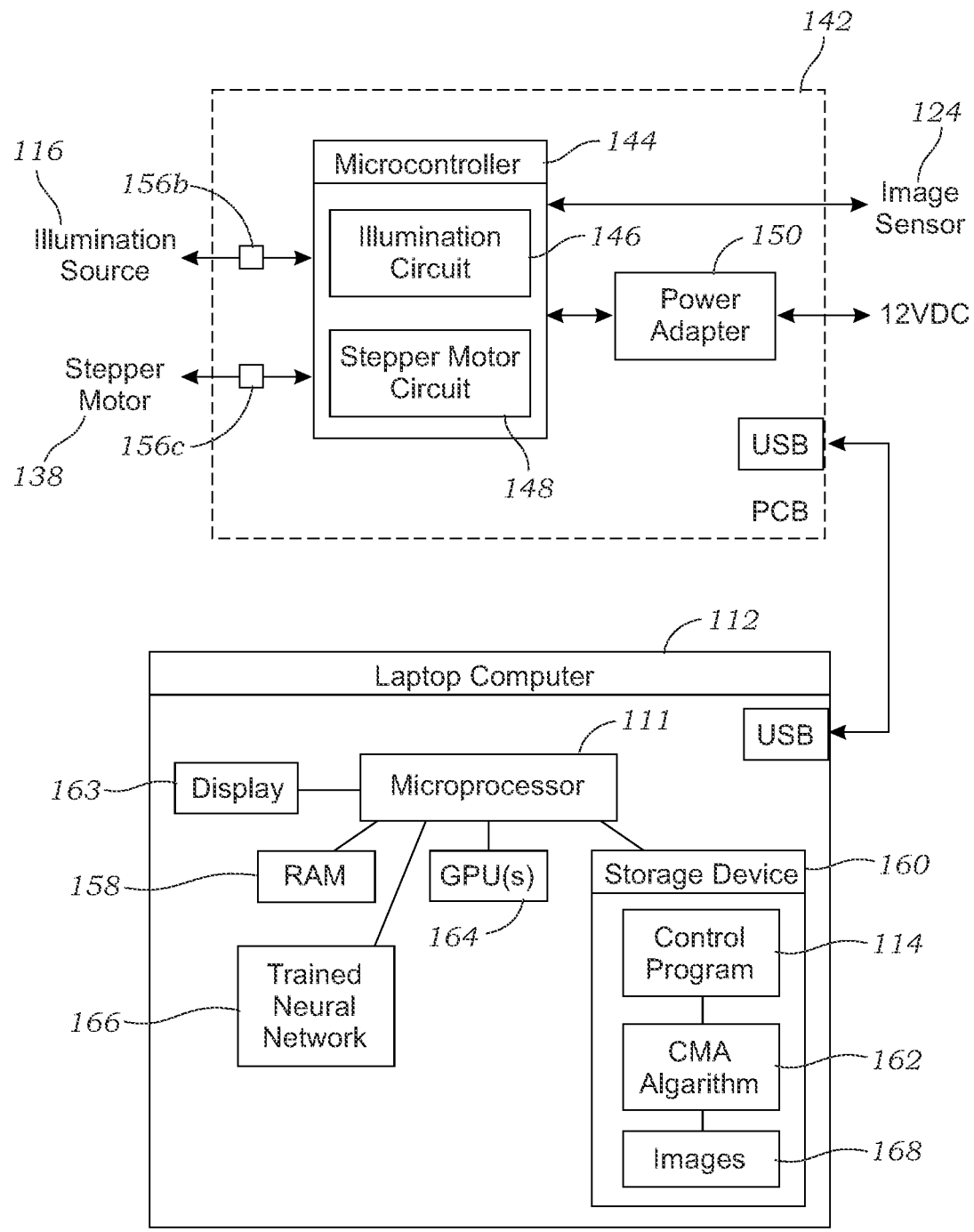
FIG. 1C is an electronic schematic diagram of the printed circuit board for the imaging platform of FIGS. 1A-1B showing selected electronic components and the interface with the computing device (e.g., a laptop computer).
Figure 2:
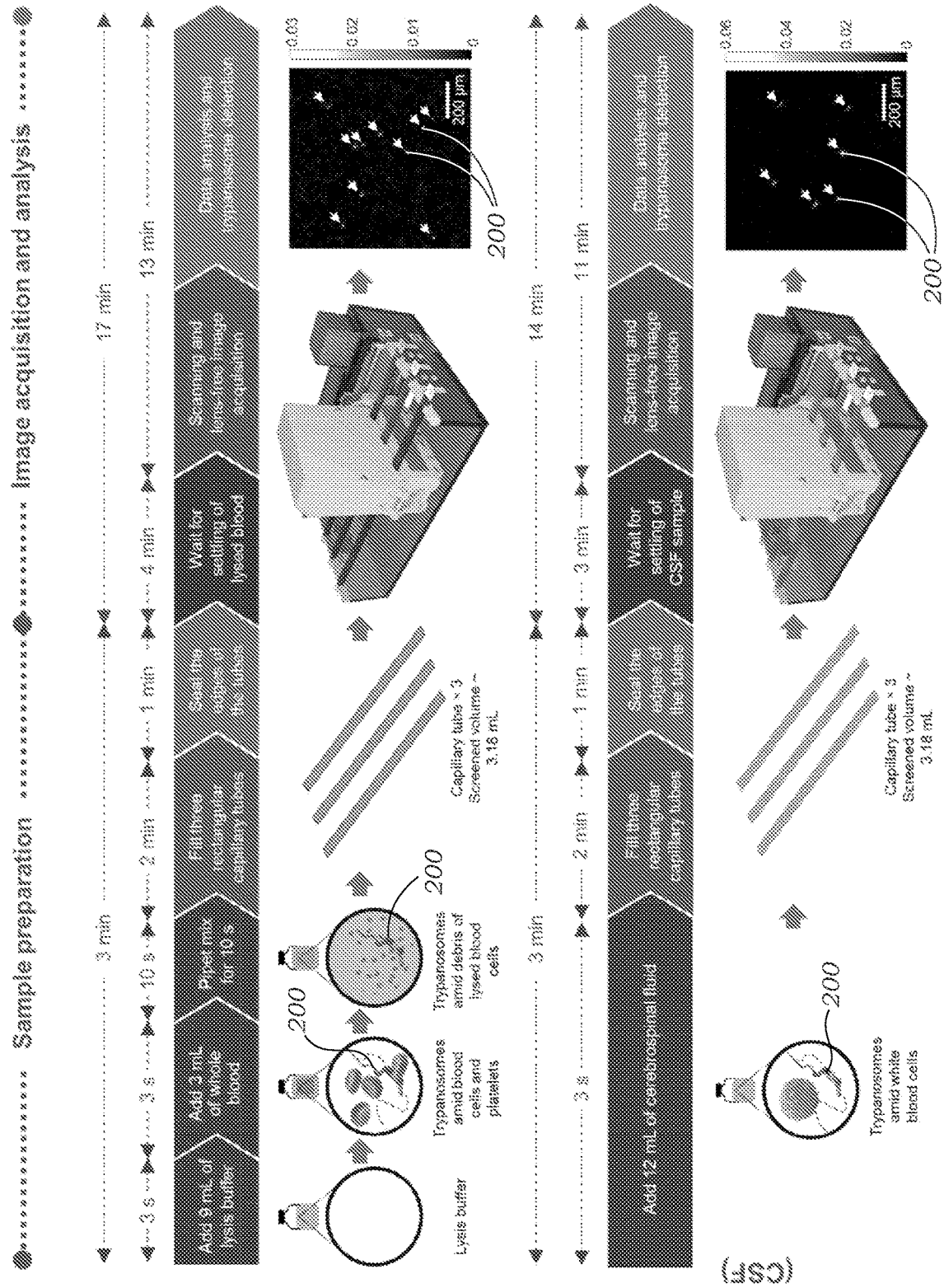
FIG. 2 is an illustration of a sample preparation and imaging process used for testing whole blood and cerebrospinal fluid (CSF) using the imaging platform of FIG. 1A, according to one embodiment of the present invention.

The present invention is directed to an imaging platform for label-free detection of motile objects 200 in a sample (see FIG. 2). FIGS. 1A-1C illustrate an imaging platform 100 for performing lensless holographic time-resolved speckle imaging of a sample 101, according to one embodiment of the present invention. The imaging platform 100 is made up of five main modules: (1) a scanning head 102 having one or more lensless holographic speckle imagers 104 (the illustrated embodiment of an imaging platform 100 shown in FIGS. 1A and 1B and described herein has three imagers 104a, 104b, 104c), (2) a translation stage 106, (3) a main housing 108 that holds the components of the imaging platform 100, (4) electronic circuitry 110 configured to control and automate various functions of the imaging platform 100, and (5) a computing device 112 having a control program 114 which provides a graphical user interface (GUI) 115. The GUI 115 is configured to enable a user to initiate the screening of a current sample in addition to various other functionalities, such as customizing image acquisition parameters, performing a live view of the diffraction patterns, taking a snapshot, querying results, sample tracking, generating reports and outputs, and stopping the acquisition.

The scanning head 102 includes one or more lensless imagers 104a, 104b, 104c housed within a scanning head housing 109 (e.g., printed by 3D-printed plastic, molded plastic, formed metal, etc.). Each lensless imager 104a, 104b, 104c includes an illumination source 116. The illumination source 116 may be a laser diode, such as a 650-nm laser diode (product no. AML-N056-650001-01, Arima Lasers Corp., Taoyuan, Taiwan) having an output power of ~1 mW, or other suitable illumination device. For instance, the illumination source 116 other than a laser diode, including a light-emitting diode (LED), another laser light source, and the like.

The emitted light 117 from the illumination source 116 passes through an optional aperture 118. The aperture 118 may be a 3D-printed aperture or other suitably constructed aperture (e.g., molded, machined, etc.). The aperture 118 functions to limit the emission angle of the emitted light and avoid light leakage into the adjacent imagers 104. The aperture 118 is optional and may not be present in all embodiments. The aperture 118 serves to prevent light leakage to the nearby image sensor 124. In embodiments where the light leakage is not an issue (e.g., where spacing or configuration of lensless imagers 104 does not suffer from light leakage), the aperture may be omitted.

The sample 101 is loaded into substantially optically transparent fluidic holders 120a 120b, 120c (also referred to as "sample holders"). The term "substantially optically transparent" means that the element is sufficiently transparent to obtain images 168 of a sample 101 through the element of sufficient quality to identify motile objects 200 in the sample 101. In one embodiment, each fluidic holder 120a, 120b, 120c is a glass capillary tube. The capillary tube may be rectangular in cross-sectional profile, or other suitable cross-sectional profile, such as circular, oval, etc.). The fluidic holder 120 is filled with the sample 101 (e.g., a bodily fluid to be screened), and is positioned a $z_1$ distance 122 below the illumination source 116. In the illustrated embodiment, the $z_1$ distance 122 is ~7 cm below the illumination source 116. Again, the aperture 118 is optional and may not be present in all embodiments. The aperture 118 serves to prevent light leakage to the nearby image sensor 124 of the adjacent imagers 104. In embodiments where the light leakage is not an issue (e.g., where spacing or configuration of the lensless imagers 104 does not suffer from light leakage), the aperture 118 may be omitted.

Each of the imagers 104a, 104b, 104c has an image sensor 124 positioned on the opposing side of the respective fluidic holder 120 from the respective illumination source 116 such that it can image a diffraction or speckle pattern of the emitted light 117 from the illumination source 116 through the sample 101 at a section of the sample 101 based on the position of the scanning head 102. For example, in the illustrated embodiment, the image sensor 124 is positioned below the fluidic holder 120, with the illumination source 116 above the fluidic holder 120. The image sensor 124 may be any suitable image sensor, such as a 10-megapixel CMOS image sensor (product no. acA3800-14 um, Basler, Ahrensburg, Germany) with a 1.67 µm pixel size and an active area of 6.4 mm×4.6 mm (29.4 mm$^2$). The image sensor 124 is positioned below the illumination source 116 a $z_2$ distance 126. The $z_1$ distance 122 is typically much greater than the $z_2$ distance. In the illustrated embodiment, the $z_2$ distance 126 (i.e., the air gap) between the image sensor 124 and the bottom surface of the fluidic holder 120 is about 1-1.5 mm, or 1-3 mm, or 0.5-5 mm, to reduce the heat transfer from the image sensor 124 to the sample 101. FIG. 1 illustrates that the $z_2$ distance 126 may be about 3 mm, in some embodiments.

Because each image sensor 124 has one or more circuit boards 125 that generate heat, heat sinks 128 are optionally inserted between the circuit boards 125 and arranged on the sides of the scanning head 102 to dissipate heat and prevent image sensor 124 malfunction and/or damage. The heat sinks 128 may be custom-made aluminum heat sinks, or other suitable heat sinks, including other materials and construction.

The embodiment used in the Examples described herein uses a scanning head 102 with three identical lensless imagers 104a, 104b, 104c that image three different capillary tubes 120a, 120b, 120c. These tubes 120a, 120b, 120c could be loaded with samples from different patients or the same patient. It should be understood that more (or fewer) lensless imagers 104 may also be used.

The translation stage 106 is configured to move the scanning head 102 in order to move the imagers 104 relative to the fluidic holders 120 so that the imagers 104 can obtain images 168 of different regions of the sample 101 contained in the respective fluid holders 120. In the illustrated embodiment, the translation stage 106 moves the scanning head 102 in a linear direction along the length of the fluidic holders 120 and is thus referred to as a linear translation stage 106. In the illustrated embodiment, the linear translation stage 106 includes two linear motion shafts 130a, 130b which are mounted to the aligned parallel to the longitudinal axis of the fluidic holders 120. The motion shafts 130a, 130b may be product no. 85421, Makeblock Co., Ltd., Shenzhen, China, or other suitable motion shafts. The linear translation stage also has two linear motion sliders 132 which are coupled, and controllably moveable relative, to the motion shafts 130a, 130b. The linear motion sliders 132 may be product no. 86050, Makeblock Co., Ltd., Shenzhen, China. The linear translation stage 106 also includes a timing belt 134 (e.g., product no. B375-210XL, ServoCity, Winfield, KS, or other suitable timing belt) operably coupled to two timing pulleys 136a, 136b (e.g., product no. 615418, ServoCity, Winfield, KS, or other suitable timing pulley) and a stepper motor 138 (e.g., product no. 324, Adafruit Industries LLC., New York City, NY, or other suitable motor) operably coupled to the timing belt 134.

The scanning head 102 is mounted onto the motion sliders 132 using screws or other suitable fasteners. The scanning head 102 with the attached motion sliders 132 moves along the stationary linear motion shafts 130a, 130b. The stepper motor 138 provides power to drive the coupled timing belt 134 and timing pulleys 136 to move the scanning head 102 back-and-forth along the linear motion shafts 130a, 130b.

While the specific linear translation stage 106 utilized and disclosed herein may be used with the imaging platform 100, it should be understood that other translation mechanisms and devices that are configured to move the scanning head 102 in a linear direction relative to the fluidic holders 120 may be used. These may include motor or servo-based devices that are mechanically coupled or linked to the scanning head 102 to impart linear movement. Likewise, the translation stage 106 may translate in different directions depending on the sample volume that is to be scanned. For example, a three-dimensional volume may be scanned in orthogonal (or other directions) to cover the sample volume. Thus, a variety of different translation motions may be used in conjunction with the translation stage 106.

The computing device 112 is configured to control the operation of the imaging platform 100. In the illustrated embodiment, the computing device 112 is a laptop computer, but the computing device 112 may include other computer-based devices (e.g., a personal computer or in some instances a tablet computer or other portable computing device). The computing device 112 may include one or more microprocessors 111, a storage device 160, a graphics processing unit (GPU) 161, and a display 163.

Referring to the schematic diagram of FIG. 1C, the electronic circuitry 110 includes a printed circuit board (PCB) 142 configured to automate the imaging platform 100. The PCB 142 includes a microcontroller 144 (e.g., a Teensy LC, PJRC) operably connected to the computing device 112 via a USB 2.0 interface (or other suitable interface). The microcontroller 144 also includes illumination driver circuits 146 (e.g., laser diode driver circuits or other suitable driver circuits), and a stepper motor driver circuit 148. The illumination driver circuits 146 may be built from constant current circuits. For instance, in the case of laser diode driver circuits, illumination driver circuits 146 may be built from product no. LM317DCYR, Texas Instruments. The stepper motor driver circuit 148 may be product no. TB6612, Adafruit, or other suitable stepper motor driver circuit.

In the illustrated embodiment, the illumination source 116 (e.g., laser diodes) and the stepper motor 138 are powered using a 12 V power adapter 150. Various digital switches 156a, 156b, 156c built from metal-oxide-semiconductor field-effect transistors (MOSFETs) are controlled by the digital outputs from the microcontroller 144 to cut the power to the laser diodes 116 and the image sensors 124 when they are unused. Specifically, to control the power to the image sensors 124, including cutting the power to the image sensor 124, the power wire of a USB 3.0 cable of the image sensor 124 is cut and a MOSFET-based digital switch 156a is inserted into the power line.

The computing device 112 contains a control program 114 that is used to control and interact with data obtained from the imaging platform 100. For example, in the specific embodiment disclosed herein, the control program 114 is a Windows®-based application written in C-Sharp programming language (C#). The control program 114 includes a GUI 115 which enables the user to initiate the screening of the current sample 101, in addition to various other functionalities, such as customizing image acquisition parameters, performing a live view of the diffraction patterns, taking a snapshot, and stopping the acquisition. It should be appreciated that other programming languages or scripts may be used as well.

Accordingly, the control program 114 controls the imaging platform 100 to obtain the time-varying holographic speckle pattern image sequences. After the sample 101 is loaded into the fluidic holders 120a, 120b, 120c on the imaging platform 100, and the sample 101 is allowed to settle for a predetermined waiting time (e.g., a waiting time of 3-4 minutes, for instance, 4 minutes for lysed whole blood and 3 minutes for artificial CSF, see FIG. 2 for details), the user presses a "record" button on the GUI 115 to start acquisition. The control program 114 is configured to program the imaging platform 100 to scan the fluidic holders 120a, 120b, 120c at a predetermined number of discrete positions to image different regions of the sample 101 within the fluidic holders 120a, 120b, 120c. For instance, in the illustrated embodiment, the imaging platform 100 may be programmed to scan the fluidic holders 120a, 120b, 120c at 36 discrete positions, with a distance of ~4.7 mm between spatially adjacent ones. This results in a total screening volume of 36 (discrete scanning positions)×29.4 mm$^2$ (FOV of the image sensor 124)×1 mm (channel height of the capillary tube 120) 1.06 mL per lensless speckle imager 104, and ~3.18 mL for the three parallel imagers combined. At each of the 36 positions, to achieve a high frame rate (~26.6 fps), the FOV of the image sensor 124 is split into two halves (i.e., the upper 1374 rows and the lower 1374 rows of the pixels), with each half capturing 61 frames (for lysed blood) or 41 frames (for CSF) sequentially (see FIGS. 9A-9D).

Figure 10A:
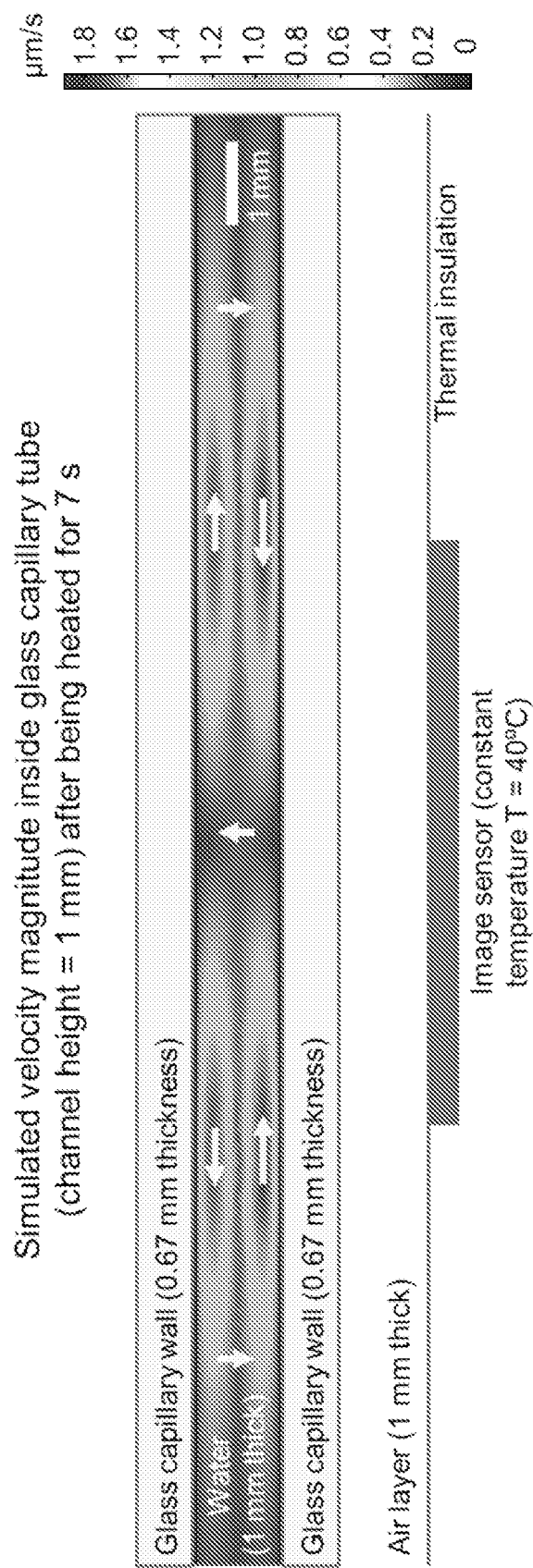
FIGS. 10A-10C illustrate the simulation of the velocity field inside the glass tube due to convection after being heated by the image sensor.
Figures 10B, 10C:
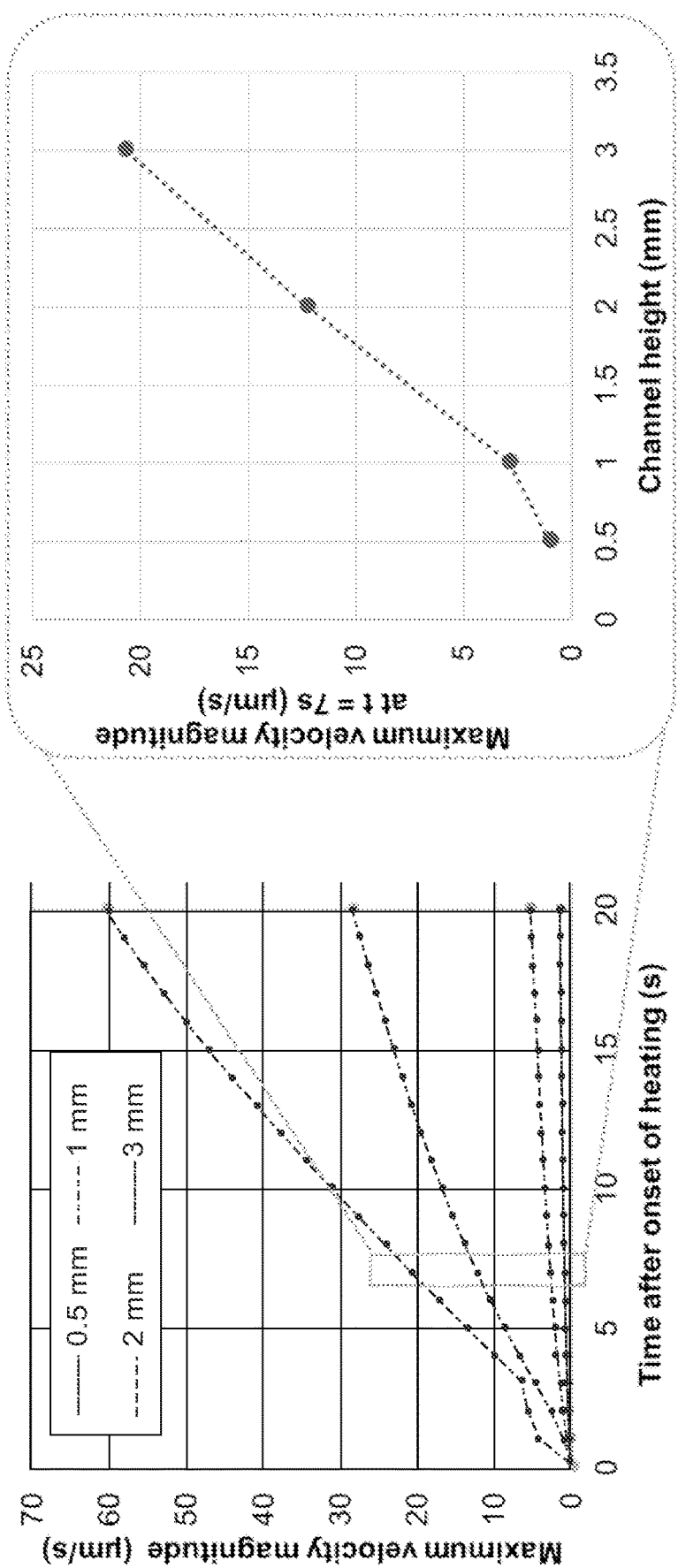
Figure 12A:
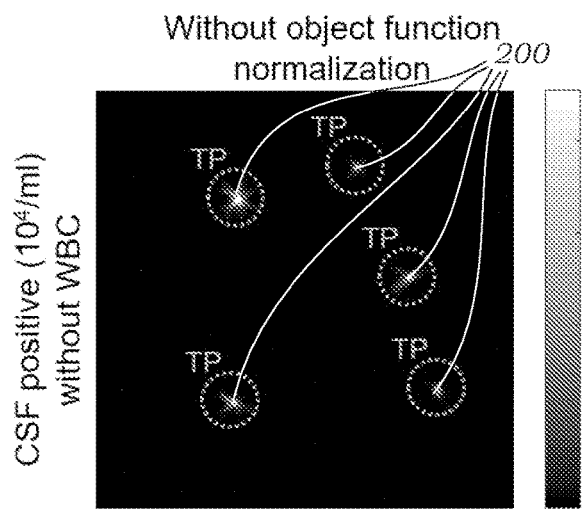
FIGS. 12A-12D are images illustrating how OFN suppresses potential "false positives" due to strongly scattering particles, demonstrated in artificial CSF. TP indicates "true positive" spots corresponding to trypanosomes; FP indicates "false positives". The false positives due to spiked WBCs that are evident in the negative control sample shown in FIG. 12C are suppressed after applying OFN as shown in FIG. 12D, whereas the true positives are preserved in the positive sample shown in FIGS. 12A and 12B.
Figure 12B:
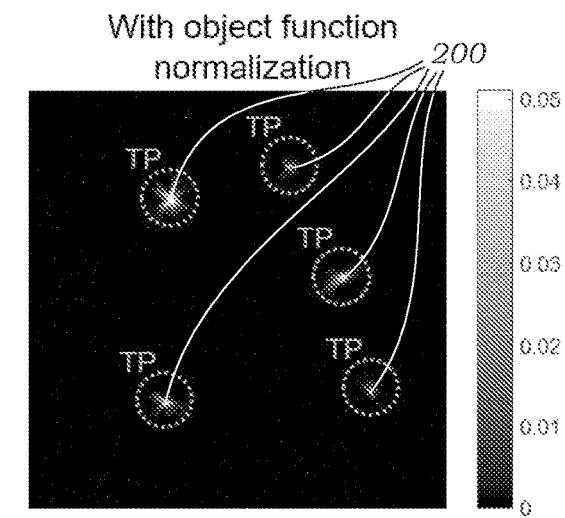
Figure 12C:
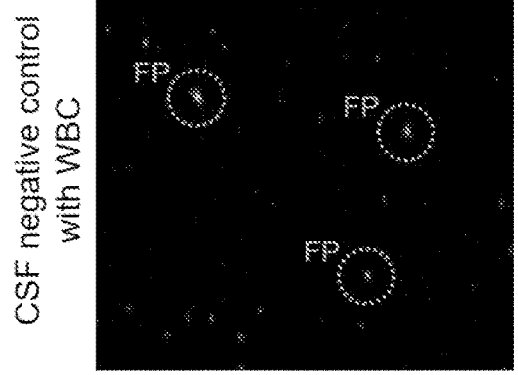
Figure 12D:
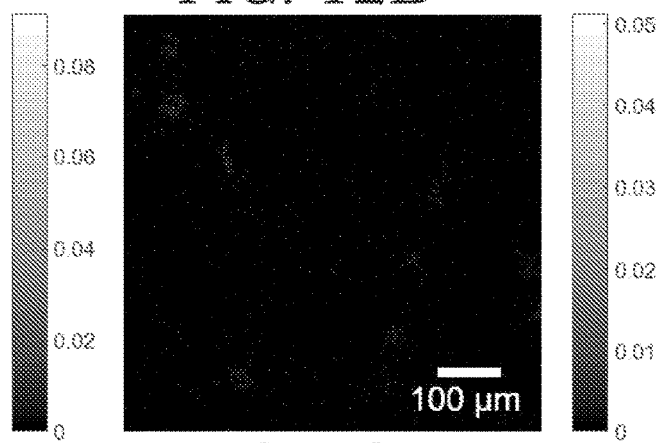

The temperature of the image sensor 124 rises when it is powered, leading to temperature gradient-induced convection flow of the liquid sample 101. An example of a temperature gradient-induced convection flow for the exemplary imaging platform 100 is illustrated in FIGS. 10A-10C. To mitigate these problems, two measures may be taken. First, instead of scanning the 36 positions unidirectionally, the imaging platform 100 may be configured to scan in a back-and-forth fashion. For example, assume the 36 positions are represented by positions #1, #2, . . . , #36, which are spatially ordered. Instead of scanning in the order of #1, #2, . . . , #36, the control program 114 programs the imaging platform 100 to scan with a larger step size of 9 positions, and whenever the scanning head 102 cannot move forward with this step size (because a step of 9 positions moves past the end positions #1 or #36), the scanning head 102 is moved to the unscanned position with the smallest position number. In other words, in this example, the imaging platform 100 first scans positions #1, #10, #19, and #28. Then, the scanning head 102 is moved back to position #2, followed by #11, #20, and #29, and so on. This scanning pattern largely prevents heat accumulation at a given section of the capillary tube 120, which has sufficient time to cool down before the scanning head 102 comes back to its vicinity. As a second measure, a predetermined "downtime" (e.g., a six (6) second "downtime", or a "downtime" from 5-10 seconds) may be added between scanning positions to allow the image sensor 124 to cool down. After completing the acquisition at a given position, the power to the image sensor 124 is cut by a MOSFET-based digital switch 156a added into the USB 3.0 cable. After the predetermined wait time (e.g., six seconds), the stepper motor 138 moves the scanning head 102 to the next position, where the power to the image sensor 124 is restored to capture the next set of images 168.

The acquired sequence of images 168 (e.g., movies or clips) are saved to the storage device 160 (e.g., a hard drive) for processing. All three image sensors 124, capturing uncompressed 8-bit images 168, generate a total data rate of ~421 MB/s, which slightly exceeds the average write-speed of a typical storage device 160 (see FIG. 1C), such as a hard drive (e.g., a solid-state hard drive (SSD)). Therefore, a queue is created in the random-access memory 158 (RAM)

for each image sensor 124 to temporarily buffer the incoming image data, and another thread is created to constantly move the image data from the buffer into the storage device 160 (e.g., an SSD). However, because all the remaining image data can be fully saved to the storage device 160 (e.g., an SSD) during the aforementioned downtime between positions, the total image acquisition time per test is not increased due to the limited write-speed. As a more time-efficient alternative, the acquired images 168 can be temporarily stored in the RAM, while they are constantly moved to the GPUs for processing in batches corresponding to each image sequence. In this way, the image processing can be performed concurrently with the image acquisition, reducing the total time per test.

A CMA algorithm 162 (e.g., programmed into CMA software 162) is utilized to generate 3D contrast data from particle locomotion in noisy holograms and speckled interference patterns and also applies deep learning-based classification to identify the signals corresponding to the parasite of interest. As an example, FIGS. 3A-3M depict an exemplary process (i.e., CMA algorithm and deep learning-based classification method) used to detect trypanosomes from lysed whole blood, whereas in other application settings (e.g., trypanosome detection in CSF), minor changes to the procedure may be applied, as explained below. The CMA algorithm 162 is configured to take the raw holographic diffraction patterns acquired by each image sensor 124 at each scanning position as input. The CMA software 162 may be used to count the number of motile species in the sample 101 which can then be used to calculate the concentration of the species of the sample 101 (given the known volume of sample). The CMA software 162 may also classify a particular sample as positive (+) or negative (−) based on the count or concentration of motile species. For example, threshold cutoff values may be used to demarcate between a positive or negative sample. The analysis results may be presented to the user on the GUI 115. In addition, movie(s) of the movement of the motile objects 200 may be viewed using the GUI 115. As noted herein, while the imaging platform 100 is particularly suited for the detection of parasites it may also be used for other motile species (e.g., sperm or other biological motile species). The samples 101 may include biological samples but may also include environmental samples in other embodiments.

Examples

Detection of Parasite Locomotion in 3D Using Holographic Speckle Analysis

To sustain a high frame rate (~26.6 fps) which is essential to the parasite detection technique, the full field of view (FOV) of each of the image sensors 124 was split in two halves, each ~14.7 mm². FIGS. 4A-4C show the raw speckle patterns of a lysed, trypanosome-spiked whole blood sample captured by the image sensor 124. Even though this simple lysis process has significantly reduced the density of the blood sample, the interference patterns (e.g., see FIGS. 4B-4C) are still highly dense due to the random light scattering resulting from the cell debris in the lysed blood. As a result, the diffraction patterns of the optically transparent and weakly scattering trypanosomes (see FIG. 4C, shown by arrows) are buried under the speckle patterns, making their direct detection extremely challenging.

To address this challenge, the spatial-temporal variations in the detected speckle patterns due to the rapid locomotion of motile trypanosomes within blood can be utilized. A CMA algorithm 162 (or CMA software 162) taking advantage of this was developed, which involves holographic back-propagation, differential imaging (with an optimally-adjusted frame interval for trypanosome locomotion), and temporal averaging, conducted at each horizontal cross section within the sample volume. Object function normalization (OFN) was introduced into each differential imaging step to suppress potential false positives due to unwanted, strongly scattering objects within the sample. The algorithm was then followed by post-image processing and deep learning-based classification to identify the signals caused by trypanosomes (see the description below for details). FIGS. 4D-4E exemplify the result of this computational process, where the "hotspots" in the processed images 168 correspond to motile trypanosomes. To better illustrate this, based on the calculated 3D locations of the three hotspots in FIG. 4E (indicated by white arrows), in-focus movies were created of the amplitude and phase channels of the back-propagated diffraction patterns. Rapid locomotion of these trypanosomes can be observed in this video, although partially obscured by the interference patterns created by the other non-motile objects (e.g., cell debris) in the sample.

Figure 6A:
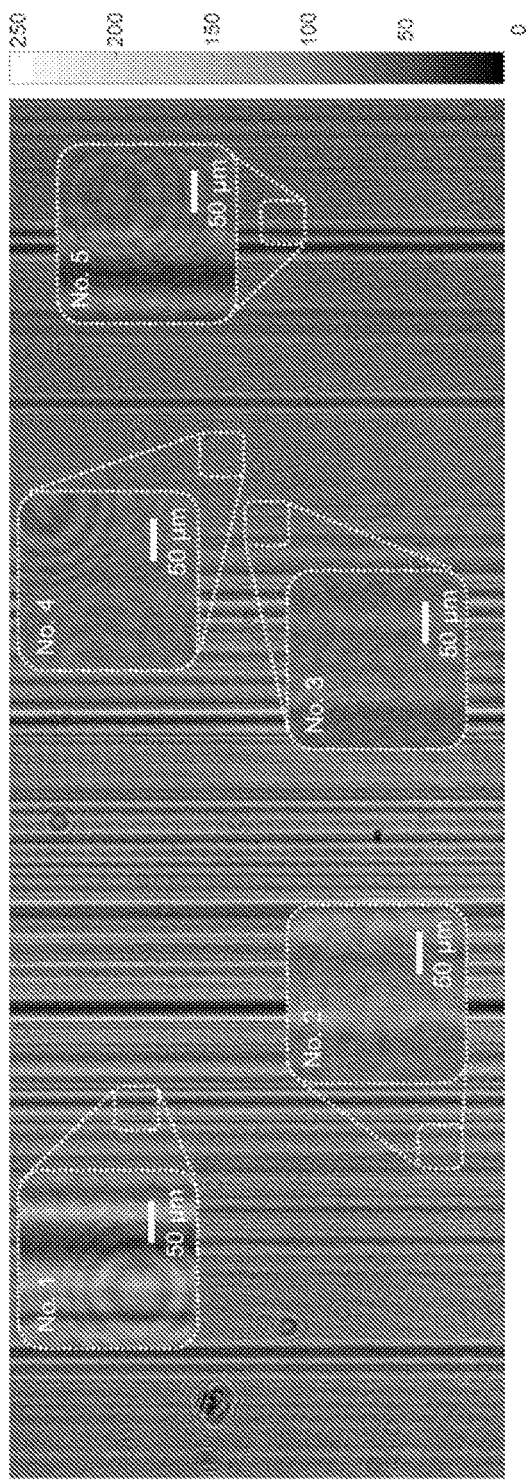
FIGS. 6A and 6B are images illustrating imaging results of trypanosomes within artificial CSF spiked with WBCs using the exemplary imaging platform.
Figure 6B:
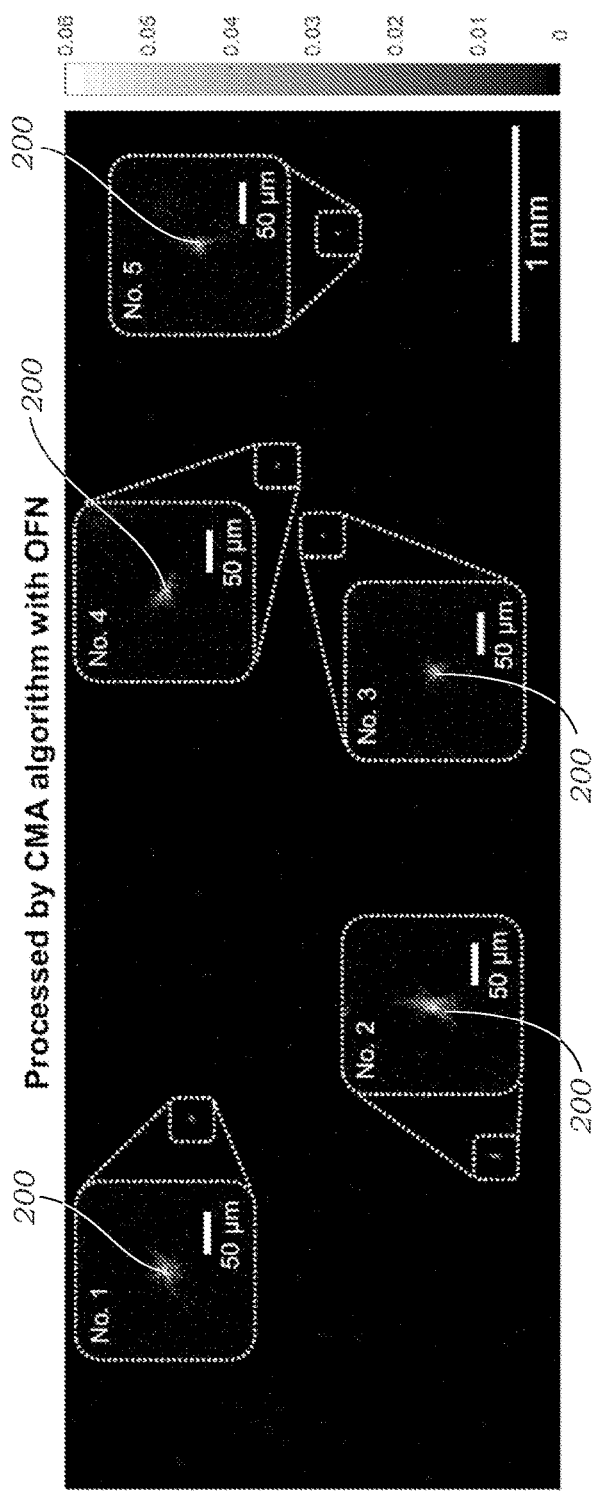
Figure 7A:
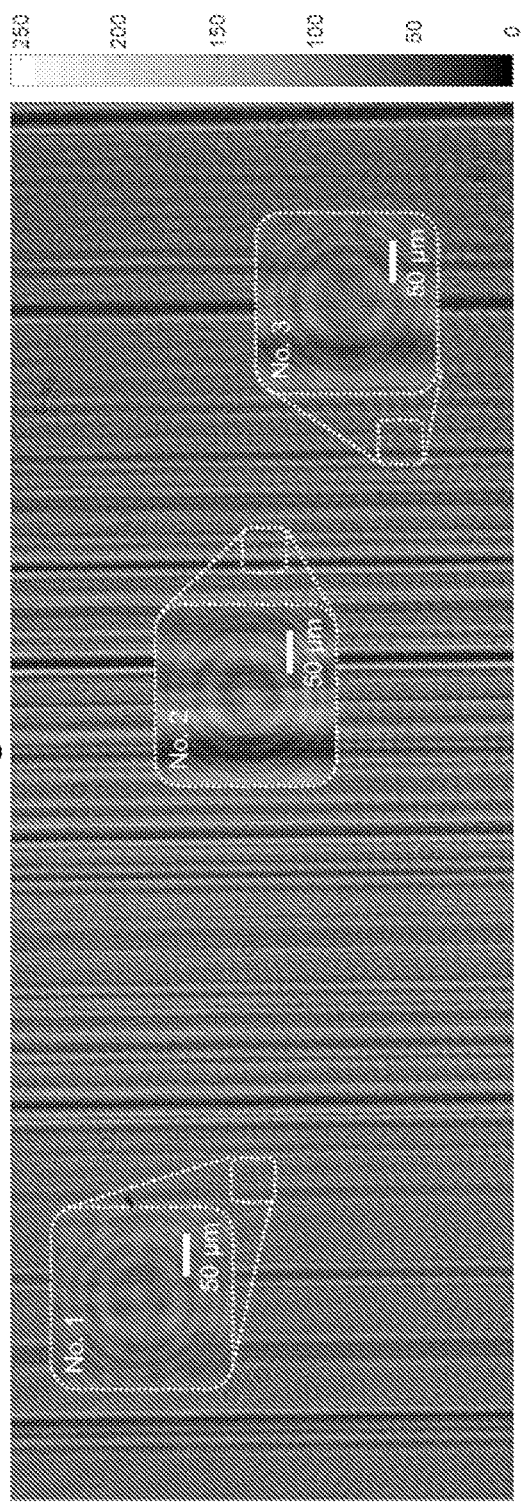
FIGS. 7A and 7B are images illustrating imaging results of *Trichomonas vaginalis* (*T. vaginalis*) within phosphate buffered saline (PBS) using the exemplary imaging platform.
Figure 7B:
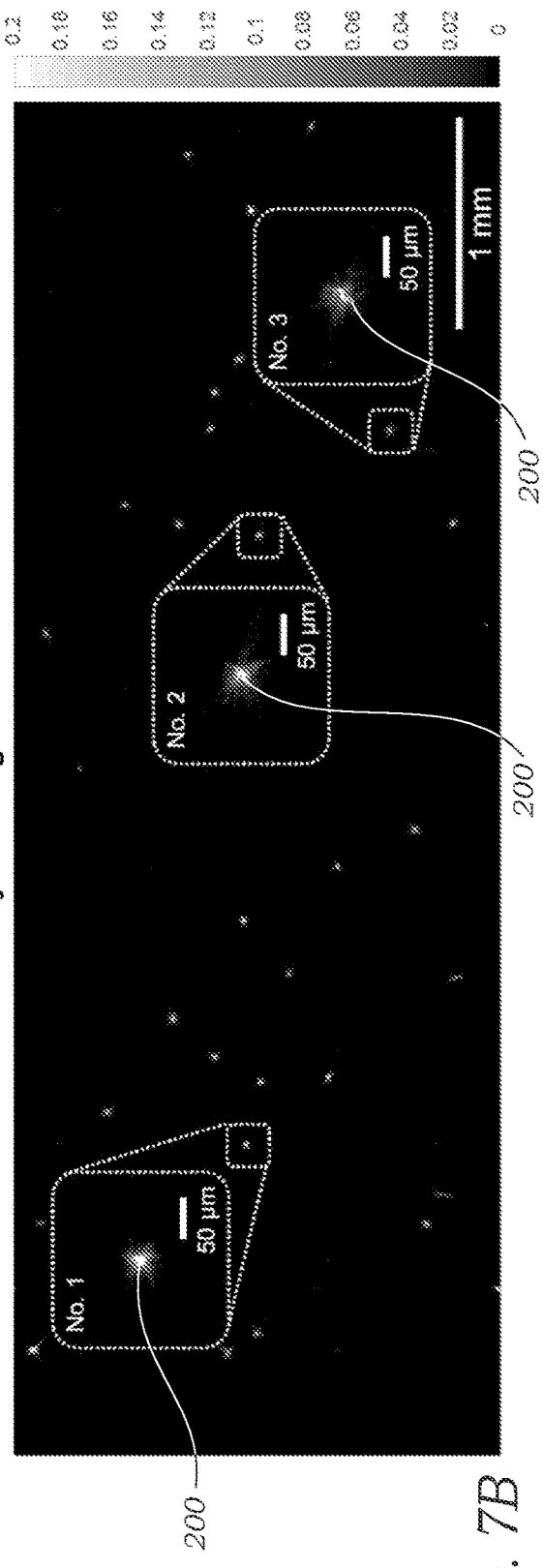
Figure 8A:
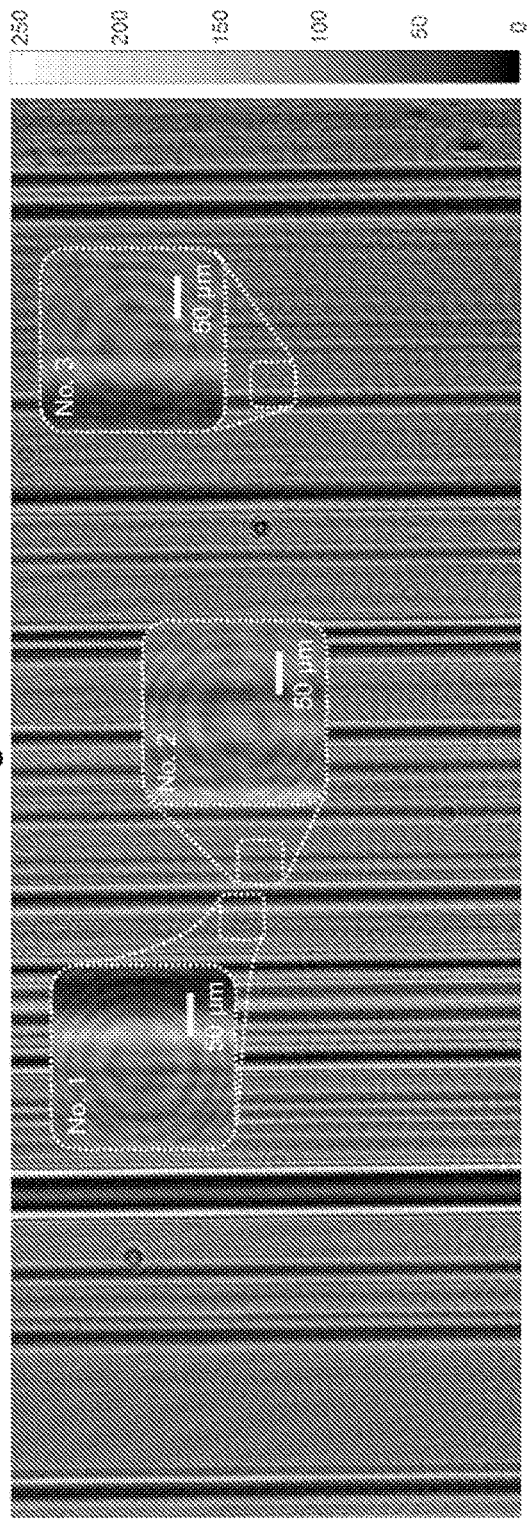
FIGS. 8A and 8B are images illustrating imaging results of *T. vaginalis* within culture medium using the exemplary imaging platform.
Figure 8B:
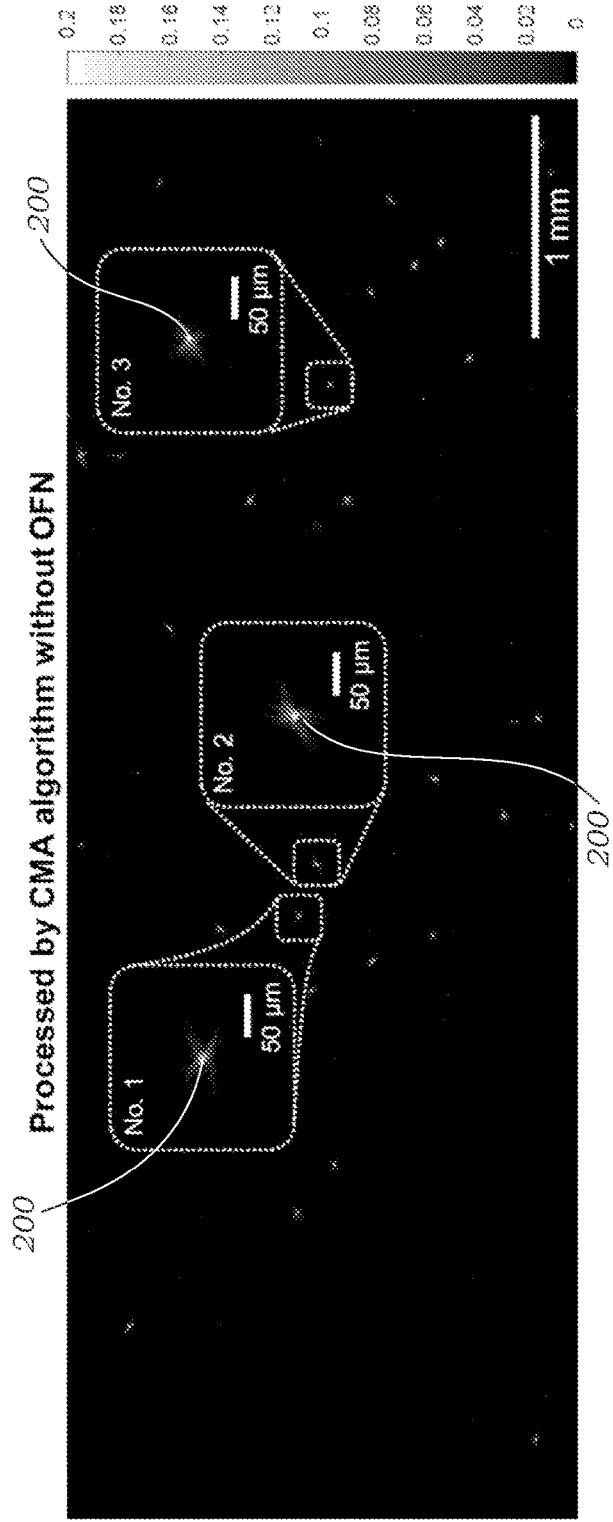

Similarly, the results of imaging trypanosomes within WBC-spiked artificial CSF samples are shown in FIGS. 6A-6B. Because CSF is mostly a clear medium, the background noise level caused by quasi-static scatterers in the medium is significantly lower compared to the motile trypanosome signal level (i.e., the hotspots in FIG. 6B). Digitally focused amplitude and phase movies also show lower-noise reconstructions of these motile trypanosomes.

As detailed in Table 1 below, >80% of the total image processing time to image and detect these trypanosomes is spent on the CMA algorithm 162, which involves thousands of fast Fourier transforms of ~6-megapixel images 168 for each recorded image sequence (see the Methods section below for details). Therefore, graphics processing unit (GPU) 164 based parallel computing is helpful for the speed-up of the CMA algorithm 162. Using a single GPU 164, the entire image processing task for one experiment (216 image sequences in total for the three parallel image sensors 124) takes ~26 minutes and ~21 minutes for blood and CSF samples, respectively. When using two GPUs 164, because each GPU 164 is given a separate image sequence to process at a given time, there is minimal interference between the GPUs 164 and maximal parallelism can be achieved. Therefore, ~2-fold speed-up is observed when using two GPUs 164, resulting in a total image processing time of ~13 minutes and ~11 minutes for blood and CSF experiments, respectively. Combined with all the other sample preparation steps, the total detection time per test amounts to ~20 minutes and ~17 minutes for blood and CSF samples, respectively (see FIG. 2 for details).

TABLE 1

| Processing step | Single GPU | | Dual GPUs | |
|---|---|---|---|---|
| | Time per image sequence (ms) Blood/CSF | Total time per test (min) Blood/CSF | Time per image sequence (ms) Blood/CSF | Total time per test (min) Blood/CSF |
| Copy data from CPU memory to GPU memory | 316.7/212.7 | 1.14/0.77 | 346.2/231.7 | 0.62/0.42 |
| Image normalization | 44.3/30.0 | 0.16/0.11 | 49.0/32.5 | 0.09/0.06 |
| Autofocusing | 523.0/NA | 1.88/NA | 680.8/NA | 1.23/NA |
| Computational motion analysis | 6205.0/5515.7 | 22.34/19.86 | 6137.8/5561.5 | 11.05/10.01 |
| Post image filtering | 106.7/136.0 | 0.38/0.49 | 108.2/138.3 | 0.19/0.25 |
| Segmentation | 10.1/10.1 | 0.04/0.04 | 10.1/10.1 | 0.02/0.02 |
| Deep learning-based classification | 9.8/10.3 | 0.04/0.04 | 9.8/10.3 | 0.02/0.02 |
| Total | 7215.6/5914.8 | 25.98/21.29 | 7341.9/5984.4 | 13.22/10.77 |

Quantification of the LoD for Trypanosomes

Figures 5A, 5B:
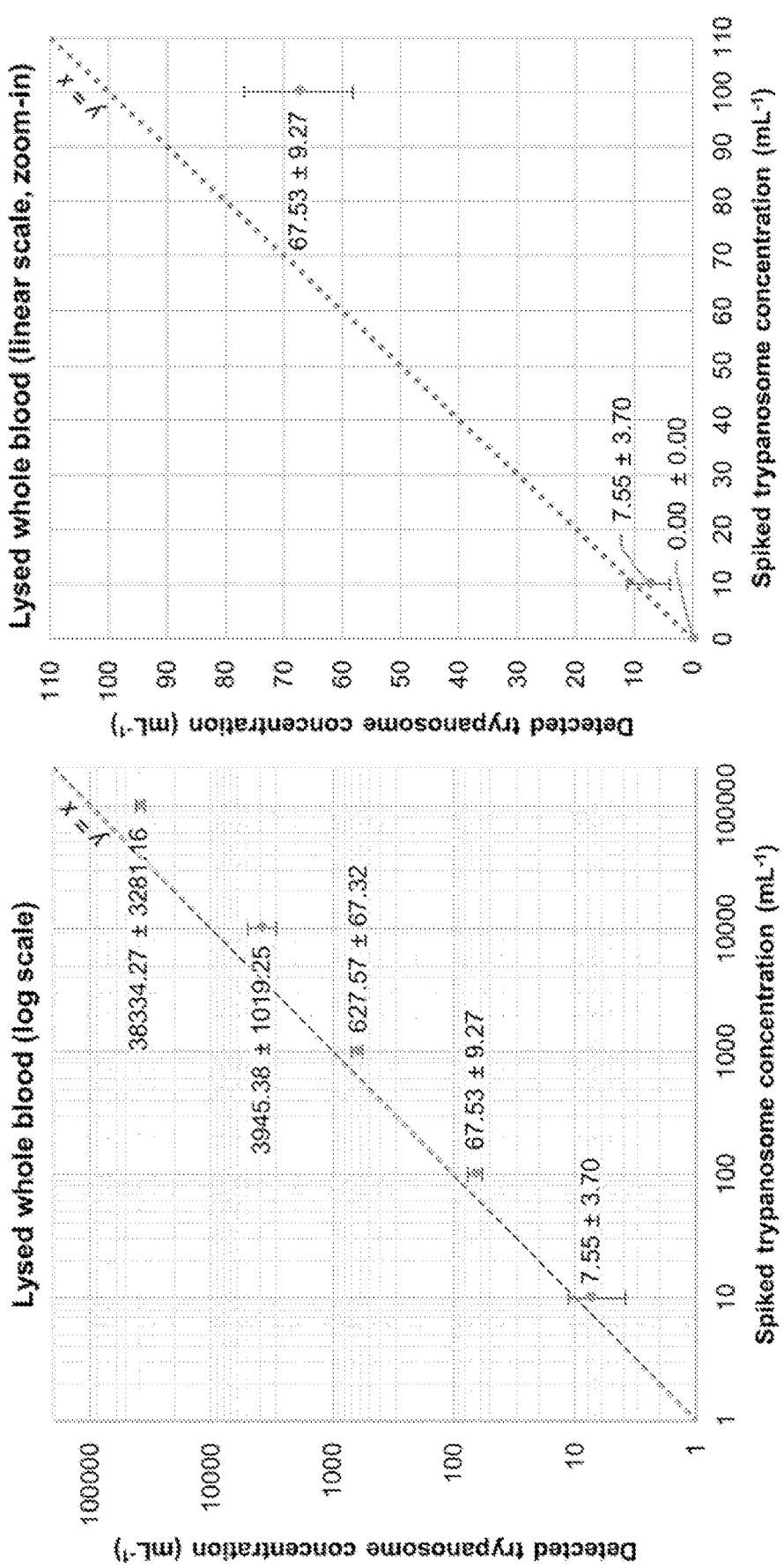
FIGS. 5A-5D are graphs illustrating the quantification of the LoD for an exemplary imaging platform constructed and tested for detecting trypanosomes in lysed whole blood and artificial CSF samples.

The LoD of the exemplary imaging platform 100 was determined for detecting trypanosomes in lysed whole blood by performing serial dilution experiments, and the results are shown in FIGS. 5A-5B. In these experiments, trypanosome-infected mouse blood was infected into uninfected blood to generate a series of parasite concentrations, including 0 mL$^{-1}$ (negative control), 10 mL$^{-1}$, 100 mL$^{-1}$, 1000 mL$^{-1}$, 10,000 mL$^{-1}$ and 100,000 mL$^{-1}$, where N=3 replicate experiments were performed at each concentration. As shown in FIG. 5A, no false positives were found in the three negative control samples, while for the three 10 mL$^{-1}$ experiments, the detected concentration was 7.55±3.70 mL$^{-1}$. Therefore, it can be concluded that the LoD is ~10 trypanosomes per mL of whole blood, which is 5× better than the best parasitological detection method currently available (i.e., the mini anion exchange centrifugation technique, mAECT, see table in FIG. 14). FIGS. 5A-5B also reveal that the recovery rate (detected trypanosome concentration divided by the spiked concentration) of the technique ranges from ~68%-76% (at the lower end of the tested concentrations) to ~38%-39% (at the higher end). This concentration-dependent recovery rate is possibly related to the proximity of trypanosomes to each other at higher concentrations, which results in more than one trypanosome in a 64×64-pixel cropped image that might be misclassified as negative by the deep learning-based classifier (see the discussion below for details), leading to underestimation of the true number of trypanosomes in the sample. This drop in the recovery rate observed at high concentrations can be potentially compensated through calibration.

Figures 5C, 5D:
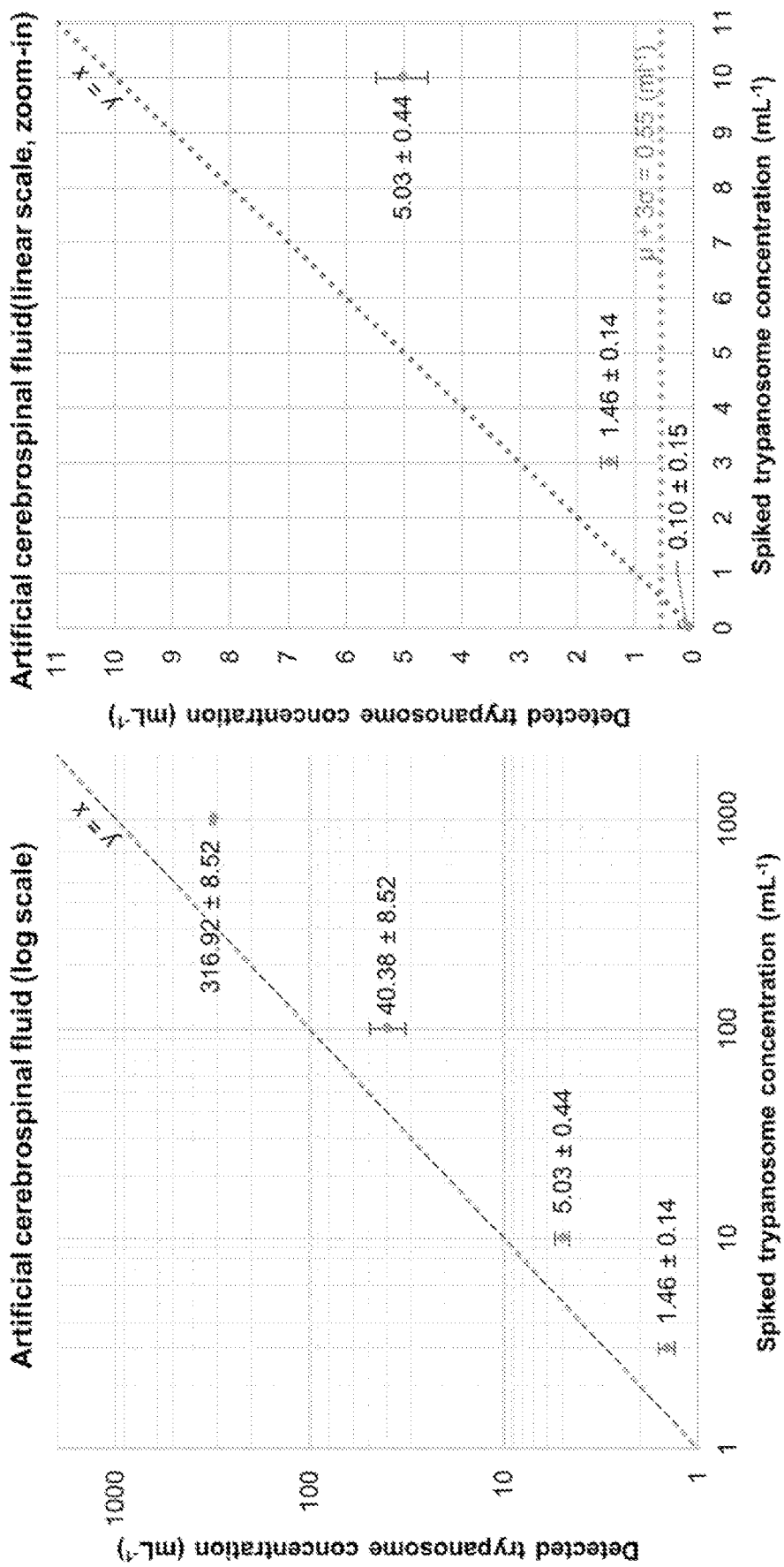

For T. brucei, stage determination is critical for determining the most appropriate treatment regimen. This is currently done by collecting CSF via a lumbar puncture and examining the CSF under a microscope. Patients with <5 μL$^{-1}$ WBCs and no trypanosomes in the CSF are classified as stage I; otherwise, if there are >5 μL$^{-1}$ WBCs or if trypanosomes are found in the CSF, they are classified as stage II. To address this need for high-throughput CSF screening, the LoD of the exemplary imaging platform 100 to detect trypanosomes in CSF was also quantified. For this purpose, an artificial CSF sample that is spiked with human WBCs was used, where cultured trypanosomes were spiked into the artificial CSF solution at concentrations of 3 mL$^{-1}$, 10 mL$^{-1}$, 100 mL$^{-1}$, and 1000 mL$^{-1}$, in addition to a negative control (N=3 for each concentration). The concentration of spiked human WBCs was selected as 20 WBCs/μL to evaluate the performance of the device to detect trypanosomes in a scenario where the WBC concentration was four times higher than the 5 μL$^{-1}$ threshold used in stage determination. Unlike the blood sample, the CSF solution is optically clear and lysis was not needed, which helped us further improve the LoD: as shown in FIGS. 5C-5D, the exemplary imaging platform 100 was able to detect trypanosomes spiked in CSF with a very low LoD of 3 trypanosomes per mL.

Detection of T. vaginalis Parasites

Although the parasite T. brucei was chosen to validate the motility-based detection approach of the imaging platform 100, it is understood that this approach is broadly applicable for the detection of a variety of motile microorganisms. As a preliminary test of the performance of the exemplary imaging platform 100 on a completely different motile parasite, T. vaginalis was selected. T. vaginalis is the protozoan parasite responsible for trichomoniasis, which is the most common non-viral STD in the United States and worldwide. T. vaginalis infects the urogenital tract of both women and men. Although often asymptomatic, T. vaginalis infection has been associated with increased risk related to other health conditions including human immunodeficiency virus (HIV) infection, pre-term labor, pelvic inflammatory disease and prostate cancer. For the diagnosis of trichomoniasis, cell culture followed by microscopy remains the best, most reliable method, as it is highly sensitive and can detect T. vaginalis from an inoculum containing as few as three parasites per mL. However, it is limited by the high cost, inconvenience, a long examination time, as well as susceptibility to sample contamination. The most common diagnostic method, wet-mount microscopy, suffers from poor sensitivity (51%-65%). Thus, the highly sensitive lensless time-resolved holographic speckle imaging method could be of substantial benefit.

With only minor adjustments to the CMA algorithm 162 (see the discussion below), it was demonstrated that the exemplary imaging platform 100 can detect T. vaginalis in phosphate-buffered saline (PBS) solution and culture medium (see FIGS. 7A-7B, 8A-8B). Based on these experiments, is can be seen that T. vaginalis creates significantly stronger signal intensities compared to trypanosomes in CSF (see FIGS. 6A-6B), which is related to the intense locomotion and strong light scattering of T. vaginalis. This suggests that the platform can potentially be used to achieve a similar, if not better, sensitivity level for T. vaginalis, e.g., reaching <3 parasites per mL. More testing may be needed to establish the LoD of T. vaginalis from different environments such as culture medium and urine, corresponding to different clinical needs, such as the detection of *T. vaginalis* from diluted vaginal secretion or directly from urine.

Discussion of Examples

A new imaging platform 100 and methods for motility-based parasite detection has been presented, based on lensless time-resolved holographic speckle imaging. The new imaging platform 100 has been demonstrated as being effective for rapid detection of trypanosomes within lysed blood and CSF, achieving an LoD that is better than the current parasitological methods (see FIGS. 5A-5D and FIG. 14). This automated technique has the potential to improve parasite screening efficiency, while reducing the need for highly specialized and expensive equipment and expertise that are essential to PCR-based or microscopic detection methods. The total cost for all the parts of the exemplary imaging platform 100 used in the Examples, excluding the laptop 112, is less than $1850; and this cost can be easily reduced to $500-1000 under large volume manufacturing. The total analysis time, including all the sample preparation steps, is only ~20 min, which is comparable to or faster than most existing methods (see FIG. 14). This motility-based method achieves high sensitivity without requiring specialized detection reagents, refrigeration, centrifugation or purification, making it more versatile for the analysis of different types of samples (e.g., blood, CSF) and is less susceptible to differences between parasite sub-species or isolates from different regions of the world. Therefore, the presented prototype could be readily adapted to any established or mobile clinic with access to electricity or battery power, representing an advancement that could be a useful addition to existing diagnostic methods.

This diagnostic method could also be beneficial for improving the diagnosis of bloodstream HAT or Chagas infection, or facilitating earlier identification of stage II HAT cases, when the parasitemia in the CSF is under the LoD of traditional methods and when the WBCs in the CSF are still scarce. The imaging platform 100 may also be useful for follow-up after disease treatment in order to screen patients for earlier and more sensitive detection of relapse. These advances could result in improved treatment outcomes for patients and increase the cure rate of disease. In addition to HAT, animal trypanosomiasis severely limits economic development. Therefore, applying motility-based detection to aid screening of infected livestock and development of vector control options could help to raise endemic areas out of poverty. In the case of Chagas disease, this technique could be adapted for screening of blood donors or blood products as well as sugarcane juice and acai juice products to help reduce various routes of transmission. Given the large populations at risk, the ability to rapidly analyze various types of samples/liquids in a simple and automated fashion will be particularly critical for developing a viable strategy to screen samples in regions where disease incidence declines owing to eradication efforts.

The imaging platform 100 and label-free detection method take advantage of the locomotion patterns of parasites to maximize the detection signal-to-noise ratio (SNR). Trypanosomes are known for their incessant motion, and motility is crucial to their survival as well as their virulence in the host. The swimming behavior of trypanosomes is highly complex. Because the flagellum is laterally attached to the cell body, parasite translocation is accompanied by cell body rotation, resulting in a "corkscrew" swimming pattern. Moreover, in addition to cell translocation, the flagellum generates rapid, three-dimensional beating patterns. The average beating frequency of *T. brucei* is estimated as 18.3±2.5 Hz in forward moving cells and 13.1±0.8 Hz in backward moving ones, whereas the rotational frequency of forward moving cells is 2.8±0.4 Hz. The frame rate that matches the average beating frequency (forward moving), according to the Nyquist sampling rate, is equal to 36.6 fps. In other words, a frame rate of at least 36.6 fps is able to record the speckle changes corresponding to each flagellar stroke; and even higher frame rates can record the speckle changes with finer time resolution, corresponding to different time points during a flagellar stroke. Assuming optimal subtraction time interval ($\Delta t$) and time window (T) are used (see discussion below, FIGS. 9A-9B), a higher frame rate leads to richer time-resolved information of speckle changes induced by motile parasites as well as more frames that can be used for averaging, thus can improve the SNR overall. However, because the goal is to generate contrast based on locomotion rather than high-fidelity recording of the beating patterns, frame rates that are below 36.6 fps are also acceptable for detection purposes. Considering the scanning time and the amount of acquired data, a frame rate of ~26.6 fps may be successfully utilized for the imaging platform 100. The performance of the imaging platform 100 may be improved using faster image sensors 100 and data interfaces to achieve higher frame rates, thereby improving the SNR without increasing the data acquisition time.

*T.b. brucei* is widely used as a model microorganism for the study of trypanosomes because it is non-pathogenic to humans and therefore safe to conduct experiments on. It is anticipated that the imaging platform 100 and methods disclosed herein will be readily applicable to *T.b. gambiense*, *T.b. rhodesiense* and *T. cruzi*, since their movements are fundamentally similar. Mouse blood and an artificial CSF solution were used throughout the testing due to safety concerns, but the lysis buffer also works with human blood. Future research may be conducted on testing patient samples from endemic regions to establish the sensitivity and specificity of the presented technique for the diagnosis of various trypanosomiases.

Figure 15:
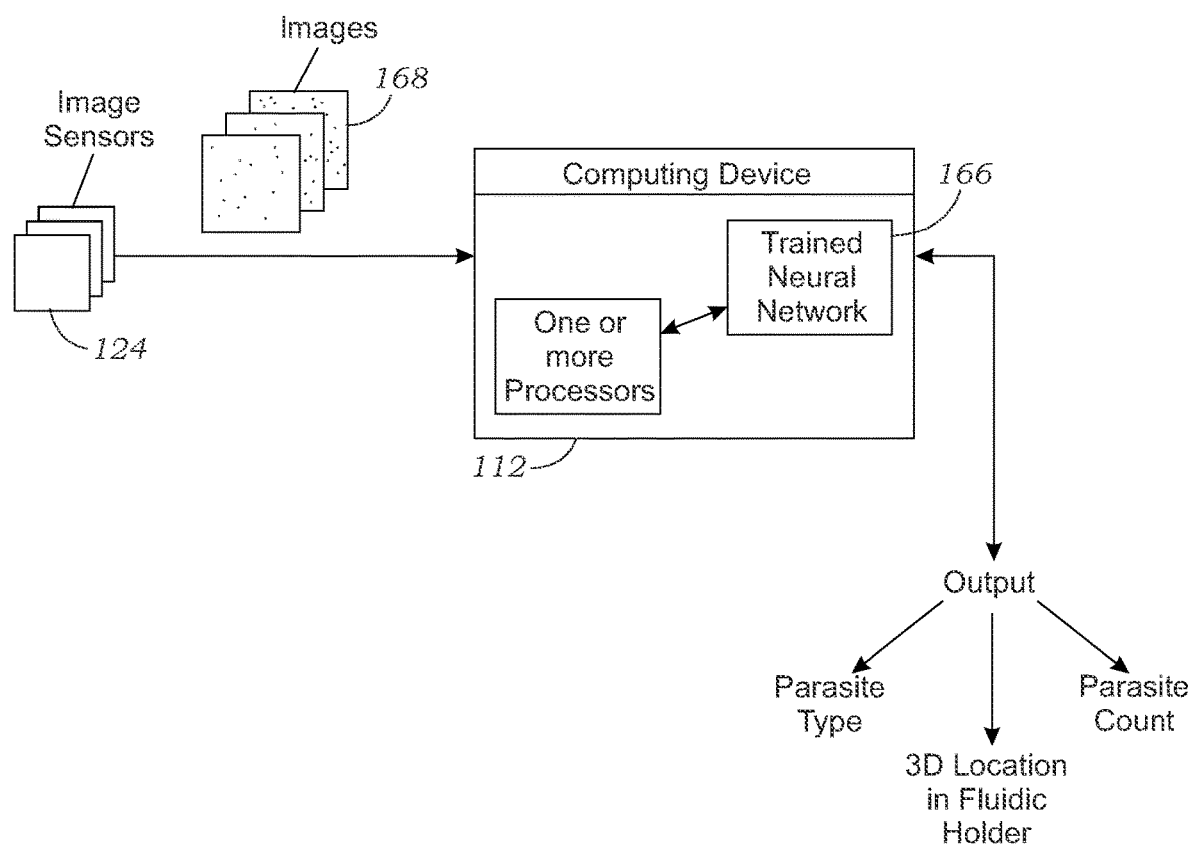
FIG. 15 is a schematic diagram of an exemplary neural network for use with the imaging platform of FIGS. 1A-1C.

Numerous motile organisms can cause infections in humans. The imaging platform 100 and disclosed methods may also be configured to automatically differentiate different parasites. For instance, the amplitude and phase movie that is generated for each detected signal (see FIG. 3M) can allow a trained clinician to distinguish different motile parasites based on the morphology, size, and motility pattern, which is analogous to observing each live parasite under a brightfield and phase-contrast microscope. These may be optionally presented to the user on the GUI 115. Prevalence of particular pathogens in the region can also aid in this regard. Moreover, a trained video classifier based on, e.g., a convolutional neural network (CNN) or a recursive neural network (RNN) can be utilized to distinguish and automatically identify various parasites, using sufficient training data. A schematic of an exemplary neural network 166 for determining characteristics of the motile parasites using the imaging platform 100 is illustrated in FIG. 15. The trained neural network 166 analyzes the sequence of images 168 and determines characteristics of the motile parasites in the sample 101, for example, the type(s) of parasites detected, 3D locations of the parasites in the 3D volume of sample 101 in the fluidic holder 120, and a count of the parasite objects.

In the Examples, trypanosomes were utilized to demonstrate the feasibility of lensless time-resolved holographic speckle imaging to be employed in detection of parasitic infection. While the approach capitalized on the motility of trypanosomes, this platform is broadly applicable to other motile parasites, including other eukaryotic parasites such as *T. vaginalis* (see FIGS. 7A, 7B, 8A, 8B), and other fluid samples beyond those tested here. in principle, this platform can also be used for the detection of *Loa loa* (*L. loa*) microfilariae in blood samples, which are significantly larger (~0.2-0.3 mm in length) compared to the parasites that we studied here. For such large motile parasites, as an alternative approach, D'Ambrosio et al. used a cellphone-based detection method by taking advantage of the displacement of the RBCs caused by the collision with *L. loa* microfilariae in an imaging chamber. (See, D'Ambrosio, M. V. et al. Point-of-care quantification of blood-borne filarial parasites with a mobile phone microscope. *Sci. Transl. Med.* 7, 286re4-286re4 (2015). This design is very compact and cost-effective, however it suffers from a much smaller detection volume (~0.01 mL) compared to the method which screens and automatically processes ~0.8 mL of whole blood or ~3.2 mL of CSF, and it would be very challenging for it to be used for the detection of parasitic protozoa such as trypanosomes which have more than an order-of-magnitude smaller size and mass, lower parasitemia, as well as much weaker light scattering compared to *L. loa*.

Motile bacteria also cause a number of human diseases. Although bacteria are typically much smaller than trypanosomes, the concept of motility-based detection combined with optical magnification may also be utilized for label-free detection of bacterial pathogens. There may be potential uses of motility-based detection for screening of other bodily fluids such as urine or diluted mucosal secretions and stool samples. Therefore, the imaging platform 100 and methods disclose herein have considerable potential to impact various global health challenges. Lastly, using motility as a biomarker and endogenous contrast can create new possibilities beyond clinical diagnostics. As a label-free 3D imaging modality that is robust to light-scattering and optically dense media, it can also be employed to study motile microorganisms within various fluid environments in a high-throughput manner.

Materials and Methods of the Examples

Sample Preparation

Lysis buffer preparation: 44 mM sodium chloride (product no. 71379, Sigma Aldrich), 57 mM disodium phosphate (product no. 30412, Sigma Aldrich), 3 mM monopotassium phosphate (product no. 60220, Sigma Aldrich), 55 mM glucose (product no. G8270, Sigma Aldrich), and 0.24% (w/v) sodium dodecyl sulfate (product no. L4390, Sigma Aldrich) in reagent grade water (product no. 23-249-581, Fisher Scientific) were mixed for 2 hours using a magnetic stir bar on a magnetic mixer. The solution was then filtered using a disposable filtration unit (product no. 09-740-65B, Fisher Scientific) for sterilization and was stored at room temperature. This buffer solution lyses all the components of whole blood including RBCs and WBCs but does not lyse the trypanosomes.

Artificial CSF preparation: According to a previous method, 1.25 M sodium chloride, 260 mM sodium bicarbonate (product no. SX0320-1, EMD Millipore), 12.5 mM sodium phosphate monobasic (product no. 56566, Sigma Aldrich), and 25 mM potassium chloride (product no. P5405, Sigma Aldrich) were mixed well, and 10 mM magnesium chloride (product no. 208337, Sigma Aldrich) was added to make 10× artificial CSF. The solution was then filtered using a disposable filtration unit for sterilization. 10× stock solution was diluted ten-fold with reagent grade water to make 1× artificial CSF.

Culturing trypanosomes: 427-derived bloodstream single marker trypanosomes (*T. b. brucei*) were cultivated at 37° C. with 5% $CO_2$ in HMI-9 medium with 10% heat-inactivated fetal bovine serum (product no. 10438026, Gibco) as described in Oberholzer, M., Lopez, M. A., Ralston, K. S. & Hill, K. L. Approaches for Functional Analysis of Flagellar Proteins in African Trypanosomes. in Methods in Cell Biology 93, 21-57 (Elsevier, 2009).

Collection of trypanosome infected mouse blood: All experiments involving mice were carried out in accordance with the guidelines and regulations of the UCLA Institutional Animal Care and Use Committee (IACUC), NIH Public Health Service Policy on Humane Care and Use of Animals, USDA Animal Welfare regulations, and AAALAC International accreditation standards under IACUC-approved protocol ARC #2001-065. Mouse infections were performed as described in Kisalu, N. K., Langousis, G., Bentolila, L. A., Ralston, K. S. & Hill, K. L. Mouse infection and pathogenesis by *Trypanosoma brucei* motility mutants. Cell. Microbiol. 16, 912-924 (2014), with the following modifications: Female BALB/cJ mice (product no. 000651, Jackson Laboratory, age 11-24 weeks) were injected intraperitoneally with $5\times10^5$-$1\times10^6$ parasites in 0.1-0.2 mL ice-cold phosphate buffered saline with 1% glucose (PBS-G). Parasitemia was monitored by counting in a hemacytometer, and infected blood samples were collected when parasitemia reached ~$10^7$-$10^8$ parasites/mL. Infected blood was collected from either the saphenous vein or by cardiac puncture after euthanasia into heparinized capillary tubes (product no. 22-260950, Fisher Scientific) or heparinized collection tubes (product no. 8881320256, Covidien).

Separation of WBCs from human blood: Ficoll-Paque PREMIUM (product no. 45-001-751, Fisher Scientific) was utilized for in vitro isolation of mononuclear cells from blood using density gradient separation according to manufacturer's instructions. Human blood samples were acquired from UCLA Blood and Platelet Center after de-identification of patients and related information and were used in the separation of WBCs from blood. 2 mL ethylenediaminetetraacetic acid (EDTA)-treated blood were mixed with 2 mL sterile PBS (product no. 10-010-049, Fisher Scientific) in a 5 mL centrifuge tube (product no. 14-282-300, Fisher Scientific) by drawing the mixture in and out of a pipette. 3 mL of Ficoll-Paque PREMIUM were placed in a 15 mL conical centrifuge tube (product no. 14-959-53A, Fisher Scientific) and the diluted blood sample was carefully layered on the Ficoll-Paque PREMIUM. The suspension was centrifuged at 400×g for 40 minutes at 19° C. using a centrifuge with swing-out rotors (Allegra X-22R, Beckman-Coulter). After centrifugation, the upper layer containing plasma and platelets was removed and mononuclear cells were transferred to a sterile centrifuge tube. To wash the cell isolate, it was mixed in 6 mL PBS and centrifuged at 400×g at 19° C. for 13 minutes. The washing step was repeated twice, and the pellet was suspended in 1 mL PBS. The concentration of WBC was determined by counting in a hemacytometer and diluted accordingly to a stock solution of $8\times10^5$ WBC/mL in PBS.

Protocol for calibration curve analysis for blood samples: Freshly collected trypanosome-infected mouse blood was diluted in uninfected mouse blood (Balb/C, female, pooled, sodium heparin, Charles River Inc.) to a concentration of approximately $10^6$ parasites/mL. A sample of this trypanosome-infected blood was lysed with 3 volumes of lysis buffer and the trypanosome concentration was determined by counting in a hemacytometer. The trypanosome-infected blood was then diluted accordingly with uninfected blood to achieve the desired concentrations for calibration curve analysis.

Protocol for calibration curve analysis for CSF samples: Cultured trypanosomes were freshly harvested for each measurement to ensure consistent parasite motility. Trypanosomes were grown to a concentration of ~1×10$^6$-1.5×10$^6$ cells/mL and harvested by centrifugation at 1200×g for 5 minutes. The cell pellet was resuspended in 1 mL of PBS-G and diluted approximately 10-fold to 10$^5$ cells/mL in PBS-G. The trypanosome concentration was determined by counting in a hemacytometer and the sample was then diluted accordingly into 1× artificial CSF to achieve the desired concentrations for calibration curve analysis.

Sample preparation for imaging: The experiments were conducted using blood and artificial CSF samples. Borosilicate capillary tubes (inner dimensions: 1 mm height×10 mm width×~30 cm length; product no. LRT-1-10-67, Friedrich & Dimmock, Inc.) were prepared by dipping one end of the capillary tube (the fluidic holders 120) into Vaseline jelly to plug the end. Plastic capillaries, e.g., those made of acrylic, can also be used instead of glass. Excess jelly was removed using a Kimwipe (product no. 06-666, Fisher Scientific) and the tube end was sealed with parafilm (product no. 13-374-12, Fisher Scientific). For each tube, 4 mL of sample was prepared. For blood samples, 3 mL of lysis buffer was mixed with 1 mL of uninfected or infected whole blood in a centrifuge tube. For CSF samples, 100 μL WBC stock solution was placed into trypanosome-infected artificial CSF to have 2×10$^4$ WBCs/mL (i.e., 20 WBCs/μL) in the final mixture. Each sample was mixed well by drawing the mixture in and out of a pipette before loading into the capillary tube. The open end of the capillary tube was then sealed using the jelly and parafilm. The glass capillary was then cleaned using a Kimwipe moistened with methanol (product no. A452SK-4, Fisher Scientific) and put on the device.

Culturing *T. vaginalis*: *T. vaginalis* strain G3 (Beckenham, UK 1973, ATCC-PRA-98) was cultured in modified TYM media supplemented with 10% horse serum (Sigma), 10U/ml penicillin-10 μg/ml streptomycin (Invitrogen), 180 μM ferrous ammonium sulfate, and 28 μM sulfosalicylic acid at 37° C.[52]. Culture was passaged daily and maintained at an approximate concentration of 1×10$^6$ cells/mL.

Design of the High-Throughput Lensless Time-Resolved Speckle Imaging Platform

As shown in FIGS. 1A-1B, the imaging platform 100 is made up of five main modules: (1) a scanning head 102 having of three lensless holographic speckle imagers 104, (2) a linear translation stage 106, (3) scanning head housing 109, (4) electronic circuitry 110, and (5) a computing device 112 having a control program 114, each of which is detailed below for the exemplary imaging platform 100 utilized in the Examples.

(1) Scanning head 102: Three identical lensless imagers 104 are built next to each other, housed by a scanning head housing 109 comprising a 3D-printed plastic using a 3D printer (Objet30 Pro, Stratasys). As shown in FIG. 1A, each lensless imager 104 uses a 650-nm laser diode (product no. AML-N056-650001-01, Arima Lasers Corp., Taoyuan, Taiwan) as the illumination source 116, which has an output power of ~1 mW. The emitted light 117 is passed through a 3D-printed aperture 118 to limit its emission angle and avoid light leakage into the adjacent imagers 104. The fluidic holders 120a, 120b, 120c each comprise a glass capillary tube filled with the sample 101 (bodily fluid) to be screened and are placed ~7 cm ($z_1$ distance 122) below the laser diode. The image sensors 124 are 10-megapixel CMOS image sensor (product no. acA3800-14 um, Basler, Ahrensburg, Germany) with a 1.67 μm pixel size and an active area of 6.4 mm×4.6 mm (29.4 mm$^2$), and are placed below the capillary tube. The air gap between the image sensors 124 and the bottom surface of the glass capillary tube is ~1-1.5 mm to reduce the heat transfer from the image sensor 124 to the sample 101. Because each image sensor 124 has multiple circuit boards 125 that generate heat, custom-made aluminum heat sinks 128 are inserted between the circuit boards 125 and arranged on the sides of the scanning head 102 to dissipate heat and prevent image sensor malfunction and/or damage.

(2) Linear translation stage 106: A linear translation stage 106 is built from two linear motion shafts 130a, 130b (product no. 85421, Makeblock Co., Ltd., Shenzhen, China), two linear motion sliders 132a, 132b (product no. 86050, Makeblock Co., Ltd., Shenzhen, China), a timing belt 134 (product no. B375-210XL, ServoCity, Winfield, KS), two timing pulleys 136a, 136b (product no. 615418, ServoCity, Winfield, KS) and a stepper motor 138 (product no. 324, Adafruit Industries LLC., New York City, NY). The scanning head 102 is mounted onto the motion sliders 132a, 132b using screws.

(3) Scanning head housing 109: The housing 109 of the scanning head 102 is made from 3D-printed plastic. The outer shell of the imaging platform (the main housing 108 of the imaging platform 100) is made from laser-cut ¼-inch acrylic sheets.

(4) Electronic circuitry 110: A printed circuit board (PCB) 142 is custom-built to automate the imaging platform 100, and includes a microcontroller 144 (Teensy LC, PJRC) connected to the laptop computer 112 via USB 2.0, laser diode driver circuits 146 built from constant current circuits (product no. LM317DCYR, Texas Instruments), and a stepper motor driver circuit 148 (product no. TB6612, Adafruit). The laser diodes 116 and the stepper motor 138 are powered using a 12 V power adapter 150. Various digital switches 156a, 156b, 156c, built from metal-oxide-semiconductor field-effect transistors (MOSFETs) are controlled by the digital outputs from the microcontroller 144 to cut the power to the laser diodes 116 and the image sensors 124 when they are unused. Specifically, to cut the power to the image sensor 124, the power wire of the USB 3.0 cable of the image sensor is cut and a MOSFET-based digital switch is inserted into the power line.

(5) Control program 114: A Windows application written in C# with a graphical user interface 115 enables the user to initiate the screening of the current sample in addition to various other functionalities, such as customizing image acquisition parameters, performing a live view of the diffraction patterns, taking a snapshot, and stopping the acquisition.

Image Acquisition

After the sample is loaded onto the imaging platform 100 and has settled for a 3-4 minutes waiting time (4 minutes for lysed whole blood and 3 minutes for artificial CSF, see FIG. 2 for details), the user presses the "record" button on the GUI 115 to start acquisition. During screening, the device is programmed to scan the capillary tubes 120a, 120b, 120c at 36 discrete positions, with a distance of ~4.7 mm between spatially adjacent ones. This results in a total screening volume of 36 (discrete scanning positions)×29.4 mm$^2$ (FOV of the image sensor)×1 mm (channel height of the capillary tube) 1.06 mL per lensless speckle imager, and ~3.18 mL for the three parallel imagers combined. At each of the 36 positions, to achieve a high frame rate (~26.6 fps), the image sensor's FOV is split into two halves (i.e., the upper 1374 rows and the lower 1374 rows of the pixels), with each half capturing 61 frames (for lysed blood) or 41 frames (for CSF) sequentially (see FIGS. 9A-9D).

The temperature of the image sensor 124 rises when powered, leading to temperature gradient-induced convection flow of the liquid sample 101 (see FIGS. 10A-10C). To mitigate these problems, the scanning position stepping method and downtime between scanning positions method, as described herein, are utilized. As described above, instead of scanning the 36 positions unidirectionally, the imaging platform 100 scans in a back-and-forth fashion. Let the 36 positions be represented by positions #1, #2, . . . , #36, which are spatially ordered. Instead of scanning in the order of #1, #2, . . . , #36, the control program 114 programs the imaging platform 100 to scan with a larger step size of 9 positions, and whenever the scanning head 102 cannot move forward with this step size, it comes back to the unscanned position with the smallest position number. That is, the imaging platform 100 first scans positions #1, #10, #19, and #28. Then, the scanning head 102 comes back to position #2, followed by #11, #20, and #29, and so on. This scanning pattern largely prevents heat accumulation at a given section of the capillary tube 120, which has sufficient time to cool down before the scanning head 102 comes back to its vicinity. As a second measure, a 6 second "downtime" is added between scanning positions to allow the image sensor 124 to cool down. After completing the acquisition at a given position, the power to the image sensor 124 is cut by a MOSFET-based digital switch 156a added into the USB 3.0 cable. After a 6 second wait time, the stepper motor 138 moves the scanning head 102 to the next position, where the power to the image sensor 124 is restored to capture the next set of images 168.

During the testing of the Examples, the acquired images 168 are saved to an SSD 160 for processing. All three image sensors 124, capturing uncompressed 8-bit images 168, generate a total data rate of ~421 MB/s, which slightly exceeds the average write-speed of the solid-state drive (SSD). Therefore, a queue is created in the RAM 158 of the laptop computer 112 for each image sensor 124 to temporarily buffer the incoming image data, and another thread is created to constantly move the image data from the buffer into the SSD. However, because all the remaining image data can be fully saved to the SSD during the aforementioned downtime between positions, the total image acquisition time per test is not increased due to the limited write-speed. As a more time-efficient alternative, the acquired images 168 can be temporarily stored in the RAM 158, while they are constantly moved to the GPUs 164 for processing in batches corresponding to each image sequence. In this way, the image processing can be performed concurrently with the image acquisition, reducing the total time per test (see Results above, FIG. 2, and Table 1).

Image Processing Using CMA and Deep Learning-Based Identification

The CMA algorithm 162 is used to generate 3D contrast from particle locomotion in noisy holograms and speckled interference patterns, and applies deep learning-based classification to identify the signals corresponding to the parasite of interest. As an example, FIG. 3 depicts the procedure used to detect trypanosomes from lysed whole blood, whereas in other application settings (e.g., trypanosome detection in CSF), minor changes are applied to the procedure, as detailed below. The CMA algorithm 162 takes the raw holographic diffraction patterns acquired by each image sensor at each scanning position as input. $A_i$ (i=1, . . . , $N_F$) are denoted as the raw frames, where $N_F$ is the total number of recorded frames in each sequence. In the experiments of the Example, the algorithm includes the following steps:

1. Hologram Preprocessing to Mitigate the Variations and Non-Uniformity of the Illumination For every 8-bit raw image acquired by each image sensor (see FIG. 3A), it is divided by a "background" intensity pattern representing the non-uniformity of the laser diode illumination source, which was previously computed from Gaussian-smoothed and averaged raw images 168 in a negative control experiment and stored to be used by other experiments. After this, the hologram is further normalized (divided) by its own mean value, yielding the illumination-corrected holograms A, (i=1, . . . , $N_F$) (see FIG. 3B).

2. Determining the Range of Axial-Distances of the Fluid Sample Under Test

In the case of lysed blood, because most of the cell debris tend to fully sediment within the 4 minute wait time (see FIG. 2), "Tamura coefficient of the gradient" (ToG) autofocusing criterion is applied to automatically determine the z-distance of the bottom of the fluid sample (see FIG. 3C), denoted as $z_b$. Then, the range of digital z-scanning as [$z_b$−200 μm, $z_b$+1200 μm] is defined with a 50 μm step size. Note that in addition to the 1 mm expected channel height, an extra scanning range of ±200 μm is given to allow for possible errors in the channel height, tilting of the channel, errors in autofocusing, etc. This makes the hardware much less complicated and inexpensive as it does not need tight tolerances in the scanning head 102 design and fluidic holder 120 placement.

In the case of clear media such as CSF where objects/particles are sparse, autofocusing to the bottom of the channel can be challenging. Therefore, the $z_b$ distance of each capillary tube is pre-calibrated (see below) and used throughout the experiments. Because the $z_b$ distance is pre-calibrated, i.e., not adaptively calculated for each sample, we specify a larger range of digital z-scanning, [$z_b$−500 μm, $z_b$+1500 μm], also with a 50 μm step size. Note that $z_b$ is slightly different for each of the three channels of the device and is calibrated respectively.

3. CMA Algorithm to Generate Contrast from Locomotion

The z-distances to be scanned are denoted as $z_j$ (j=1, . . . , $N_z$) as determined by the previous step. each element of is digitally propagated to each of $z_1$ with a high-pass filtered coherent transfer function (see FIG. 3D; see below for details) to obtain $$B_{i,j} = HP[S(\bar{A}_j, z_j)] \quad (1)$$

where S # represents the angular spectrum-based back-propagation, HP represents high-pass filtering, and i=1, . . . , $N_F$, j=1, . . . , $N_z$.

Next, time-averaged differential analysis with OFN is applied (see FIG. 3E), which yields:

$$C_j = \frac{1}{N_F - \delta_F} \sum_{i=1}^{N_F - \delta_F} \frac{|B_{i+\delta_F, j} - B_{i,j}|}{\exp\left[\gamma \cdot \frac{1}{2}|B_{i+\delta_F, j} + B_{i,j}|\right]} \quad (2)$$

where $\delta_F$ is the subtraction frame interval, $\exp[\gamma \cdot \frac{1}{2}|B_{i+\delta_F}B_{i,j}|]$ is the OFN factor, γ is a parameter related to OFN that is respectively tuned for lysed blood (γ=2) and CSF experiments (γ=3). Time-averaging significantly improves the SNR by smoothing out random image noise as well as random motion of unwanted particles/objects while preserving the true signals of motile microorganisms. OFN further suppresses potential false positive signals resulting from e.g., strongly scattering, unwanted particles/objects such as cell debris (see below and FIGS. 11A-11F, and 12A-12D). The result of this step, $C_j$, is a three-dimensional image stack.

4. Post-Image Processing and Segmentation

The z-stack $C_j$ (j=1, ..., $N_z$) suffers from a low-spatial-frequency background that mainly results from high-frequency noise in the raw images 168, which remains when performing high-pass filtered back-propagation and frame subtraction. Therefore, as shown in FIGS. 3F-3H, the 3D z-stack $C_j$ is first high-pass filtered in the z-direction by a mean-subtracted Gaussian kernel ($\sigma_z$=250 μm) and the negative pixels are clipped to zero, yielding $D_j$ (j=1, ..., $N_z$). It is then projected into a 2D image, E, using maximum intensity projection (MIP). High-pass filtering is applied again in 2D (mean-subtracted Gaussian kernel, $\sigma_x=\sigma_y$=25 μm) to remove the residual background, and the negative pixels are again clipped to zero, yielding F.

Segmentation of candidate signal points within F is performed by 2D median filtering (3×3 pixel window, pixel size=1.67 μm), thresholding (threshold=0.01 for detecting trypanosomes in lysed blood and 0.02 for detecting trypanosomes in CSF) followed by dilation (disk-shape structuring element, radius=2 pixels, pixel size=1.67 μm) and searching for connected pixel regions. Connected regions that are smaller than 5 pixels are discarded. 64-by-64 pixel image patches centered around the pixel-value-weighted centroids of these connected regions are cropped from F (without 2D median filtering), and are used for the downstream identification by a deep learning-based classifier.

5. Deep Learning-Based Classifier for Detection of Motile Trypanosomes

Figure 13:
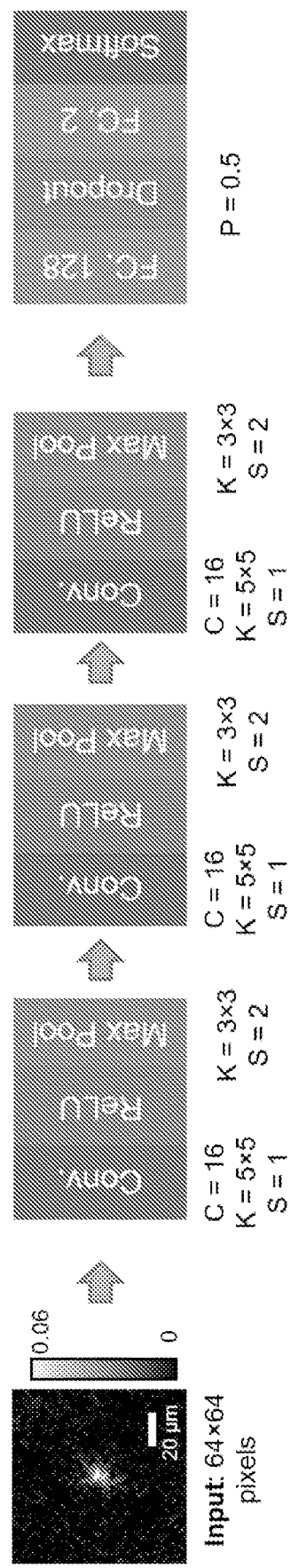
FIG. 13 is a graphic illustrating the structure of the convolutional neural network (CNN) to automatically detect the signals created by trypanosomes. In the graphic of FIG. 13, C is the number of channels; K is the convolutional filter size; S is the stride; and P is the probability of dropout.

A CNN that consists of three convolution blocks followed by two fully-connected layers is built and trained to identify true signal spots created by motile trypanosomes. The detailed network structure is shown in FIG. 13, which is separately trained for trypanosome detection from lysed blood and CSF samples (see "Construction and training of the convolutional neural network (CNN) for the identification of trypanosomes" below for details).

6. Generation of Test Results

The image processing steps (see FIGS. 3A-3J) are repeated for each captured image sequence and each image sensor 124. The total detected number of trypanosomes from all the positions are summed up and divided by the total screened volume (~3.18 mL) to calculate the detected parasitemia. For lysed blood, it is further multiplied by a factor of 4, i.e., the dilution factor introduced by lysis, to calculate the parasitemia in the original whole blood sample.

7. 3D Localization of Motile Microorganisms and Movie Generation

The technique also offers the capability to locate the motile microorganisms in 3D and generate in-focus amplitude and phase movies of them for a close-up observation, using the following steps. For each signal spot that is classified as positive by the CNN classifier, using the corresponding z-stack $D_j$ (j=1, ..., $N_z$), only a "column" that is 30×30 pixels in x-y, centered around this spot, while spanning the entire z-range ($N_z$ layers) is cropped out. Then, an autofocusing metric is used to evaluate each of the $N_z$ layers, and the layer that corresponds to the maximum value of the autofocusing metric corresponds to its in-focus position. Both ToG and Tamura coefficient-based criteria were tried, and both work very well for this purpose. While the current z-localization accuracy is limited by the z-step size we chose ($\Delta z$=50 μm), it can be further improved through finer z-sectioning. Using the currently found z-localization distance as an initial guess, high-pass filtered back-propagation and differential analysis (detailed in Step 3 CMA Algorithm, above) is performed over a z-range of ±100 μm around the initial guess with a finer z-step size of 5 μm. However, OFN is disabled this time; in other words, the exponential normalization factor in Eq. 2 is removed, owing to OFN's side effect of slightly weakening the signal at the optimal focus distance, where the object function of the microorganism is the strongest. Autofocusing is performed again over the same 30×30-pixel region over different z-layers similarly as before. The previously determined x-y centroid, in addition to the newly found z-distance, is used as the 3D location of this motile microorganism. Because the additional high-pass filtered back-propagation and differential analysis may be only performed on a smaller region-of-interest (ROI) around each given spot (e.g., in the experiments described herein, an ROI of 512×512 pixels is used), the 3D localization is computationally efficient. The 3D localization capability can be used to generate movies (detailed below), or to study microorganism behavior in biological or biomedical research settings.

Using the obtained 3D position of each motile microorganism, the movie of each detected microorganism can be generated by digitally back-propagating (without high-pass filtering) each frame of the recorded raw image sequence $A_i$ (i=1, ..., $N_F$) or the illumination-corrected version $\overline{A}_i$ to the corresponding z-coordinate. The amplitude and phase channels of the back-propagated images 168 are displayed side by side. The generated movies can potentially be used as an additional way to confirm the detection result of this platform when trained medical personnel are available.

Timing of Image Processing Algorithm

Here, a laptop 112 equipped with an Intel Core i7-6700K central processing unit (CPU) 111 @ 4.00 GHz, 64 GB of RAM was used, and two Nvidia GTX 1080 GPUs 164 for image processing. Table 1 summarizes the time required for the image processing workflow, using a single GPU 164 or using two GPUs 164 simultaneously. Here, it is assumed that during image acquisition, the images 168 captured by the imaging device 124 are temporarily stored in the CPU RAM 158 and are constantly moved to the GPU memory in batches corresponding to the scanning positions, where it is processed by the GPU 164 (or GPUs). In this way, image processing can be performed concurrently during image acquisition, shortening the time requirement per test. This situation is mimicked by pre-loading existing data from the hard drive 160 into the RAM 158 of the computer 112 before starting the timer, which provides a reasonable estimation of the time cost of the processing. Because the number of acquired images 168 and the image processing workflow for lysed blood and CSF are different (see previous subsections and Methods), their timing results are calculated individually. In Table 1, timing results for lysed blood and CSF are separately by "/".

Pre-Calibration of the z-Distance Range

To pre-calibrate the z-distance range for each of the three channels of the imaging platform 100, one capillary tube whose bottom outer surface was purposely made dirty was installed. Then, three holograms was captured when the scanning head is at the two ends of its scanning range as well as in the middle, and autofocused to the dirty surface using the three holograms respectively[53, 54]. The expected $z_b$ in this case was calculated from the averaged autofocusing distance by adding the wall thickness of the glass capillary tube. The calibration step needs to be done only once.

High-Pass Filtered Computational Back-Propagation

The diffraction patterns are back-propagated to the given z-distances using the angular spectrum method, involving a 2D fast Fourier transform (FFT), a matrix multiplication in the spatial frequency domain with the free-space transfer function, and an inverse FFT. However, because the approximate size of the trypanosomes is known, a high-pass filter is added into the transfer function in the spatial frequency domain to suppress other noises and artifacts.

The coherent transfer function of free-space propagation is given by $$H(f_x, f_y; z) = \begin{cases} \exp\left[j\frac{2\pi z}{\lambda}\sqrt{1-(\lambda f_x)^2-(\lambda f_y)^2}\right], & \sqrt{f_x^2+f_y^2} \leq \frac{1}{\lambda} \\ 0, & \text{others} \end{cases} \quad (3)$$

where z is the propagation distance, $\lambda$ is the optical wavelength, $f_x$ and $f_y$ are spatial frequencies in x and y, respectively.

On top of H, two high-pass filters, $H_1$ and $H_2$, are added to suppress unwanted interference patterns. $H_1$ is a 2D Gaussian high-pass filter, which is used to suppress the low-frequency interference patterns owing to the reflection from the various surfaces in the light path, including the protective glass of the image sensor and the various interfaces of the capillary tube loaded with fluids. $H_1$ is given by $$H_1(f_x, f_y) = 1 - \exp[-\tfrac{1}{2}\sigma_1^2(f_x^2+f_y^2)] \quad (4)$$

where $\sigma_1 = 25.05$ μm. $H_2$ is used to suppress the interference patterns caused by the unwanted grooves of the manufactured glass capillary tubes. Because the grooves are oriented along the axial direction of the capillary tubes, corresponding to the y-direction in the captured images, their energy is mostly concentrated close to the $f_x$ axis in the spatial frequency domain. Therefore, $H_2$ performs high-pass filtering to $f_y$, which is given by $$H_1(f_x, f_y) = 1 - \exp[-\tfrac{1}{2}\sigma_1^2(f_x^2+f_{y'}^2)] \quad (5)$$

where $\sigma_2 = 116.9$ μm.

The final coherent transfer function, which combines H, $H_1$ and $H_2$, is given by $$\tilde{H}(f_x,f_y;z) = H(f_x,f_y;z) \cdot \min\{H_1(f_x,f_y), H_2(f_x,f_y)\} \quad (6)$$

where $\min\{H_1, H_2\}$ chooses the smaller filter value from $H_1$ or $H_2$.

Optimization of the Subtraction Frame Interval $\delta_F$ and Total Analyzed Frames $N_F$ in the Computational Motion Analysis (CMA) Algorithm with Object Function Normalization (OFN)

The subtraction frame interval $\delta_F$ and total analyzed frames $N_F$ are parameters that should be optimized for the parasite (or microorganism) to be detected. $\delta_F$ and $N_F$ are related to the subtraction time interval $\Delta t$ and the total analyzed time T through $$\delta_F = \Delta t \cdot R \quad (7)$$

$$N_F = T \cdot R \quad (8)$$

where R is the frame rate of the recorded sequence (i.e., 26.6 fps in the system). By optimally choosing $\delta_F$ (or $\Delta t$), the signal from the characteristic locomotion of the microorganism of interest can be amplified with respect to the noise, which includes image sensor noise in addition to unwanted random motion of the background objects/particles in the sample. $N_F$ (or T), on the other hand, determines the window of time-averaging. A larger $N_F$, in general, will result in reduction of the random background noise through averaging; but at the same time, it can potentially also weaken the useful signal if the microorganism swims away from its original location during T due to directional motion.

$\delta_F$ and $N_F$ are optimized for trypanosome detection by evaluating the average signal-to-noise ratio (SNR) of the processed images by CMA with OFN (corresponding to FIG. 3H), for blood and cerebrospinal fluid (CSF). Signal is defined as the maximum value of the segmented hotspot, whereas noise is defined as the average value of the background, excluding signal regions. SNR is calculated as $20 \cdot \log_{10}(\text{Signal/Noise})$ (dB). 20 hotspots were randomly chosen from one imaged field of view (FOV) of a $10^4$/mL trypanosome-spiked blood experiment, and 40 hotspots were randomly chosen from a $10^4$/mL trypanosome-spiked artificial CSF experiment. The SNRs were averaged for blood and CSF, respectively. $\delta_F$ and $N_F$ are varied to observe their effects on average SNR (see FIGS. 9A-9D). The same set of hotspots were used consistently for average SNR calculations as we varied $\delta_F$ and $N_F$ for either blood and CSF, respectively.

Figures 9A, 9B:
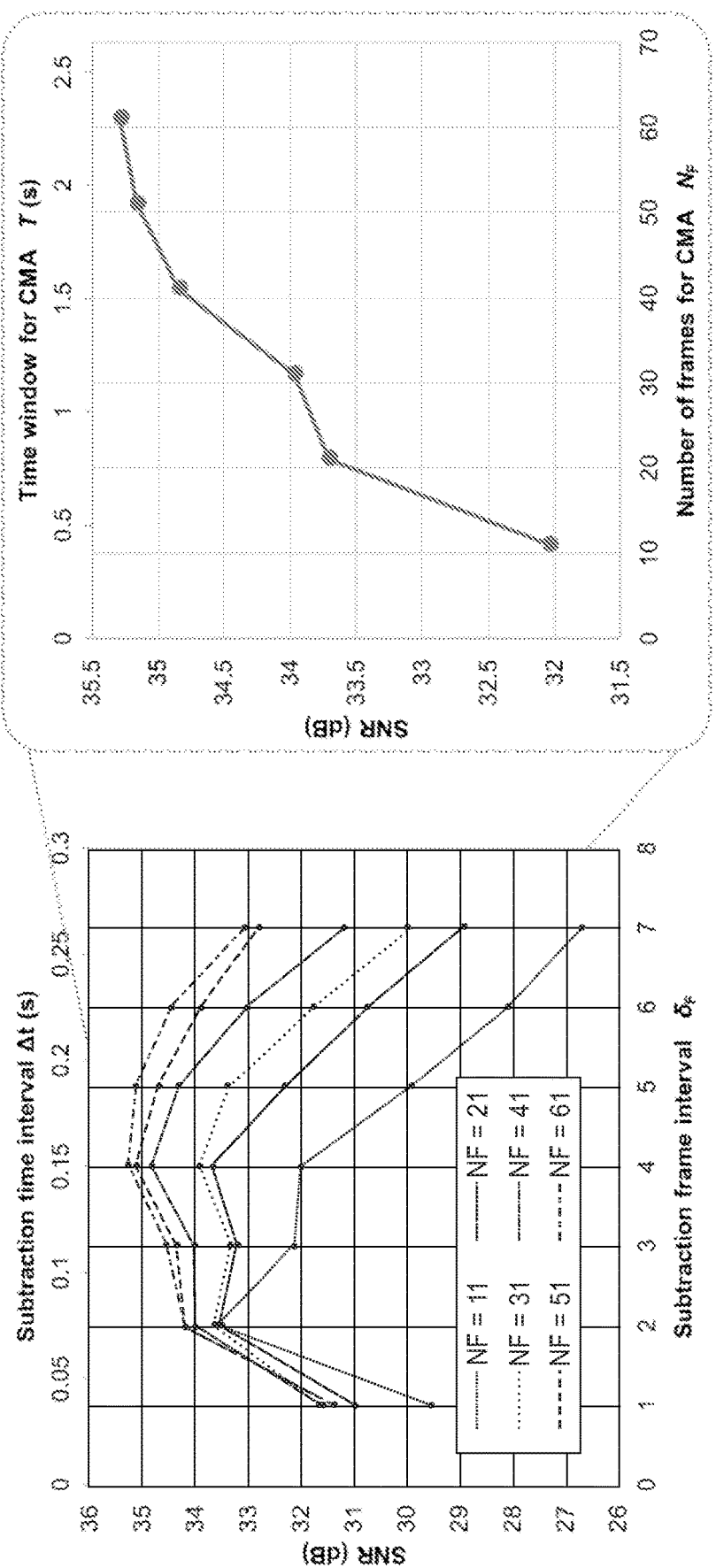
FIGS. 9A-9D are graphs illustrating the optimization of the subtraction frame interval $\delta_F$ and total analyzed frames $N_F$ for differential analysis. The signal-to-noise ratio (SNR) is used as the criterion for optimization.

As shown in FIGS. 9A-9B, for lysed blood, $\delta_F=4$ ($\Delta t=0.15$ s) and $N_F=61$ frames (T=2.29 s) leads to the highest SNR of 35.29 dB. FIG. 9B implies that the average SNR could still increase if a larger $N_F$ (T) is used. However, due to practical time constraints of this platform as a diagnostic tool as well as heating of the sample over time, only 61 frames per image sequence are recorded.

Figures 9C, 9D:
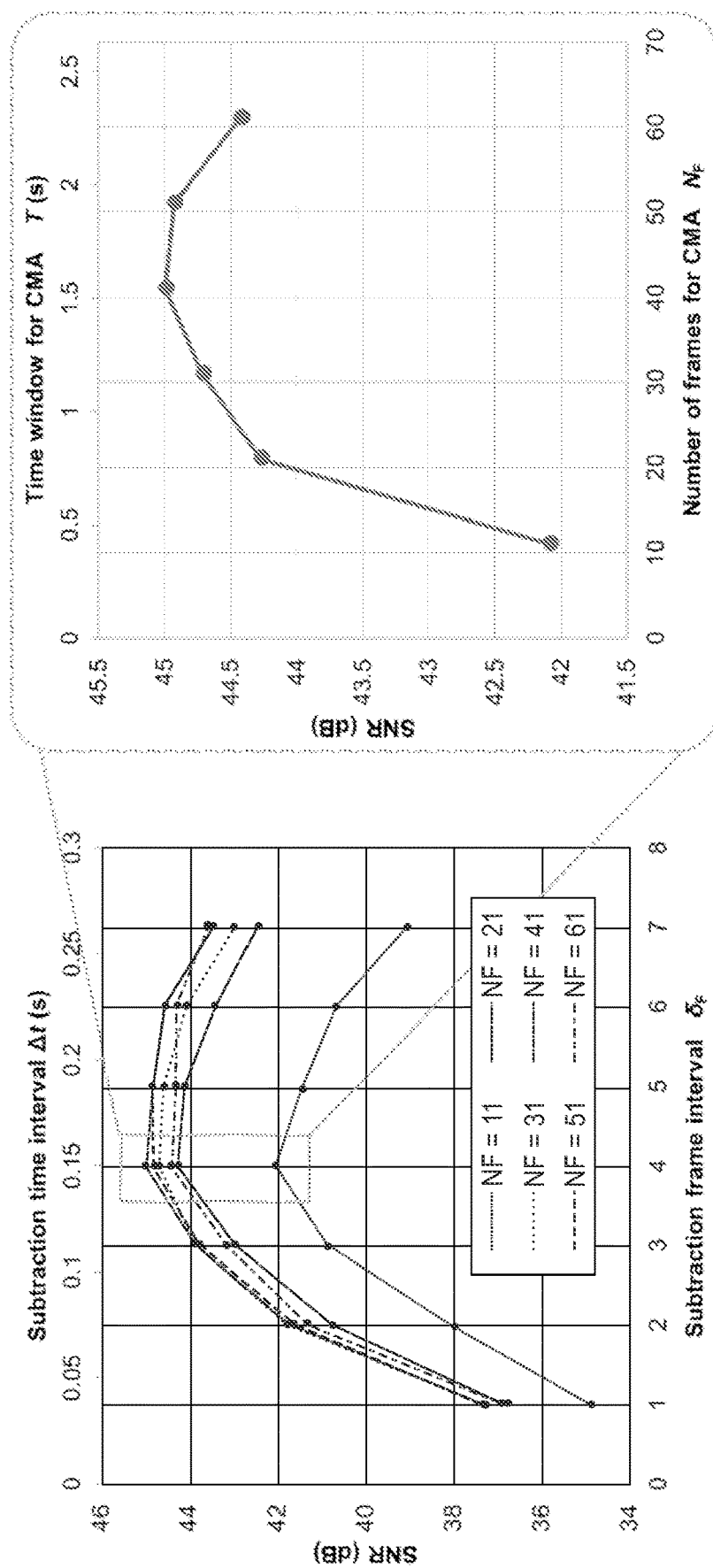

For CSF (see FIGS. 9C-9D), a similar effect is observed regarding $\delta_F$, which maximizes the SNR at $\delta_F=4$. However, FIG. 9D shows that the SNR drops as a function of $N_F$ when $N_F>41$, and therefore, the optimal $N_F$ is chosen as $N_F=41$. In addition, the optimal SNR for CSF ($\delta_F=4$, $N_F=41$) is 45.00 dB, which is ~10 dB higher than the optimal SNR in blood. Based on these observations, it can be concluded that because CSF is a clear medium (as compared to the lysed blood), less averaging (i.e., a smaller $N_F$) is needed to achieve a low noise and high SNR. Therefore, for $N_F$ beyond 41, the benefit in SNR from more averaging is diminished, whereas other factors that decrease SNR start to become dominant, mainly due to the gradual displacement of microorganisms from their original locations.

Object Function Normalization (OFN) to Remove Potential False Positives

OFN is essential to reduce potential false positives owing to strongly scattering particles/objects within the sample (see FIGS. 11 and 12 for a comparison of results with and without OFN). Under slightly time-varying illumination and drifting of the fluid, strongly scattering particles/objects such as cells that are not lysed, clumps of cell debris, spiked white blood cells (WBCs) in the CSF samples or even air bubbles can create strong contrast (hotspots) when processed by CMA. These hotspots can resemble those created by trypanosomes, leading to false positive detections. Therefore, in order to distinguish parasites of interest (especially trypanosomes) that have weak scattering and strong locomotion from other unwanted objects that have strong scattering and weak locomotion, we use the object function itself to normalize the frame subtraction corresponding to Eq. 2. An exponential function with a properly selected γ further selectively suppresses strongly scattering objects. For trypanosome detection in lysed blood, γ=2 is chosen based on visual judgement of the resulting distinction between "true positive" signals versus potential "false positive" signals; for trypanosome detection in CSF, γ=3.

Construction and Training of the Convolutional Neural Network (CNN) for the Identification of Trypanosomes Generation of Positive Images for Training/Validation Positive images are manually identified from experimental data with a relatively high concentration of spiked trypanosomes. For blood, one test (i.e., one scanning experiment with three capillary tubes) with a spiked trypanosome concentration of ~$10^4$/mL was used (no overlap with the data reported in FIG. 5). For CSF, one test with a spiked trypanosome concentration of ~$10^4$/mL in artificial CSF was used, and the sample was not spiked with WBCs as was done for testing. For each bodily fluid type, the images were processed using the CMA algorithm 162 with OFN followed by post image filtering and segmentation (see description herein for details), and movies were generated for the first 4000 detected candidate spots. Two human annotators jointly viewed these movies and judged the existence of a motile trypanosome in each movie characterized by a slender body and rapid beating. The resulting label for each movie was either "positive" (with a high confidence that there existed a moving trypanosome), "negative", or "uncertain". Multiple trypanosomes that co-exist in a single video are labeled as "negative" to avoid confusing the network during training. It was much easier to annotate the movies related to CSF due to the high quality of the holographic reconstruction in the clear medium; whereas for blood, the resulting labels were mostly either "positive" or "uncertain", because it was difficult to affirm that the movie did not contain a trypanosome. After manual annotation, only those that were labeled as "positive" were kept in training/validation. The "uncertain" and "negative" were discarded. This resulted in 3697 positive images for blood and 3890 positive images for CSF. Note that the movies are solely for the purpose of labeling, and the 2D maximum intensity projection (MIP) image patches resulting from CMA are used to construct the training/validation library. The images were then randomly split into training and validation sets using a four-to-one ratio. Finally, data augmentation was performed to increase the number of training images by mirroring the images horizontally, vertically, and both horizontally and vertically, resulting in 4× larger positive training libraries for blood and CSF, respectively.

Generation of Negative Images for Training/Validation

Negative training/validation images entirely came from negative control experiments (no overlap with the data reported in FIG. 5). One negative control test was used to populate the training/validation library for blood; two negative control tests were used for CSF because of fewer "false positives" per test. When segmenting the negative images, a lower intensity threshold was used (0.008 for blood and 0.015 for CSF) to generate more images, resulting in 5834 negative images for blood and 2586 images for CSF experiments. The images were randomly split into training and validation sets using a four-to-one ratio for blood and CSF, respectively. Data augmentation was performed to the negative training libraries similarly to the positive set by mirroring the images in three different ways, resulting in a 4× enlargement of the negative training library size. In addition, to improve the robustness of the trained classifier to unseen data, we also performed augmentation by replicating the negative images and multiplying by a factor of 1.5. Thus, the total enlargement factor for the negative training libraries is 8×.

Network Architecture

A CNN 166 was constructed with three convolutional blocks and two fully connected (FC) layers (see FIG. 13). Each convolutional block consists of a convolutional layer (filter size=5×5, stride=1, 16 channels) followed by a rectified linear unit (ReLU) layer and a max-pooling layer (filter size=3×3, stride=2). The first FC layer has 128 output nodes, and the second FC layer has 2 output nodes, representing the two classes (trypanosome and non-trypanosome). The outputs are then passed through a softmax layer to generate the class probabilities. Dropout (p=0.5) is added to the first FC layer during training. The same network architecture is separately trained to identify trypanosome signals within blood and CSF.

Network Training

The CNN 166 was implemented in TensorFlow (version 1.7.0) and Python (version 3.6.2). The convolutional kernels were initialized using a truncated normal distribution (mean=0, standard deviation=$5.5 \times 10^{-3}$). The weights of the FC layers were initialized using the Xavier initializer. All network biases were initialized as zero. The learnable parameters were optimized using the adaptive moment estimation (Adam) optimizer with a learning rate of $10^{-3}$. A batch size of 64 was used, and the network was trained for ten thousand iterations until converged.

CUDA Acceleration of the CMA Algorithm

The CMA algorithm 162 was accelerated using CUDA C++ and was run on a laptop computer 112 with dual Nvidia GTX 1080 graphics processing units 164 (GPUs). The most computationally intensive mathematical operations in the CMA algorithm 162 were fast Fourier transforms (FFTs) and inverse FFTs (IFFTs). The Nvidia CUDA Fast Fourier Transform library (cuFFT) library was used to perform these operations. Thrust library was used to perform reduction (i.e., summation of all elements) of an image, which was further used to calculate the mean value of the image for normalization. Other various basic mathematical operations on real or complex-valued images were implemented using custom-written CUDA kernel functions. The CUDA code was carefully optimized to parallelize computation, maximize efficiency and minimize GPU memory usage. For instance, when performing back-propagation of the diffraction patterns to each z-distance, the high-pass-filtered coherent transfer function (Equations 3-8) was only calculated once per z-distance, which was reused for all the frames in the time sequence. When performing time-averaged differential analysis with OFN (Eq. 2), only ($\delta_F$+1) back-propagated images (i.e., $B_i$) needed to be stored in the GPU memory at each given time without sacrificing performance, which reduced the GPU memory usage and made it possible to process even larger-scale problems (e.g., image sequences with more frames, or performing CMA at more z-distances) or to use lower-end GPUs with less memory.

Before performing FFTs, the raw images 168 (vertical: 1374 pixels, horizontal: 3840 pixels) were padded to a size of 1536×4096 pixels. The padded pixels were assigned the mean value of the unpadded image to reduce artifacts from discontinuities. Because the new dimensions are powers of 2 and 3 (1536=$2^9$×3 and 4096=$2^{12}$), the FFT operation was accelerated by a factor of ~2.4× compared to without padding. After IFFT was complete, the images 168 were cropped back to the original size for other image processing steps.

COMSOL Simulation of Sample Heating Due to the Image Sensor

The temperature of the image sensor 124 rises when it is turned on, creating a temperature gradient above it. Therefore, the fluid sample 101 within the glass tube 120 will gradually start to flow, also causing the particles within the glass tube to move directionally. As a result, the signal of motile microorganisms generated by the CMA algorithm 162 will weaken due to a "smearing" effect; and in the meantime, the movement of the other unwanted particles will increase the background noise and false positive detections, which is undesirable. The fluid sample 101 velocity due to convection is related to the height of the fluid channel. Due to the drag force near the channel wall, a thinner channel will lead to a reduced fluid velocity at a given time after the onset of heating. However, as a tradeoff, a thinner channel also results in a reduced screening throughput.

COMSOL Multiphysics simulation software was used to estimate the flow speed inside the channel. As shown in FIG. 10A, a channel (1 mm inner height, 10 mm inner width, surrounded by a silica wall with a uniform thickness of 0.67 mm) filled with water was created. A 6 cm section of the channel was selected as the region of interest for simulation. At the center of the channel, a CMOS image sensor 124 (modeled as a constant heat source with a surface temperature of 313 K) was placed 1 mm below the channel's bottom surface. ~313 K was the highest temperature of the image sensor 124 during image acquisition (see Methods), experimentally measured by an infrared camera (FLIR C2). The reference temperature (room temperature) was set to be 293 K. Non-isothermal flow was used to model the water inside the channel and the air outside the channel.

FIGS. 10B-10C show the result of this simulation. The maximum fluid velocity magnitude inside the channel is shown, representing a worst-case scenario. As expected, the fluid velocity increases as a function of the time after onset of heating and the channel height (see FIG. 10B). The relation between the maximum fluid velocity and the channel height in (c), at t=7 s after the onset of heating was further plotted, which approximately corresponds to the duration of image acquisition (there is a time gap when switching from the upper half to the lower half of the image sensor's FOV). Again, the fluid velocity at t=7 s represents a worst-case scenario, where the fluid velocity is largest. As shown in FIG. 10C, at a channel height of 1 mm, the fluid velocity is ~2.9 µm/s. Over the duration of a single image sequence of 61 frames (~2.3 s), the displacement due to fluid flow is upper-bounded by ~6.7 µm, which is acceptable when compared with the length of the trypanosome. On the contrary, if the channel height is 2 mm, the displacement will be upper-bounded by ~28 µm, which will lead to strong smearing and reduction of the signal. As a result, the channel height used in the experiments conducted herein was chosen as 1 mm.

While embodiments of the present invention have been shown and described, various modifications may be made without departing from the scope of the present invention. The invention, therefore, should not be limited, except to the following claims, and their equivalents. Thus, various changes and modifications may be made to the disclosed embodiments without departing from the scope of the following claims. For example, not all of the components described in the embodiments are required, and alternative embodiments may include any suitable combinations of the described components, and the general shapes and relative sizes of the components may be modified. Likewise, dimensional and other limitations found in the drawings do not limit the scope of the invention.

What is claimed is:

1. An imaging platform for the label-free detection of motile objects in a sample comprising:
   one or more substantially optically transparent sample holders;
   a moveable scanning head containing one or more coherent light sources and corresponding image sensor(s) associated with the one or more coherent light sources, wherein no lens is present between the one or more coherent light sources and the corresponding image sensor(s);
   a translation stage configured to translate the moveable scanning head along the one or more optically transparent sample holders;
   a computing device configured to receive time-varying holographic speckle pattern image sequences obtained by the image sensor(s), the computing device comprising computational motion analysis software configured to generate a three-dimensional (3D) contrast map of the motile objects within the one or more optically transparent sample holders that back-propagates the time-varying holographic speckle pattern image sequences followed by differential analysis, image filtering, and thresholding to find connected regions, the computing device further comprising a deep learning-based classifier software to identify motile objects in the three-dimensional (3D) contrast map.

2. The imaging platform of claim 1, wherein the sample comprises a biological fluid.

3. The imaging platform of claim 2, wherein the biological fluid comprises blood.

4. The imaging platform of claim 2, wherein the biological fluid comprises cerebrospinal fluid.

5. The imaging platform of claim 1, wherein the one or more optically transparent sample holders comprise one or more capillary tubes.

6. The imaging platform of claim 1, wherein the scanning head contains one or more light sources selected from the group consisting of laser diodes, light-emitting diodes, and lasers, projecting light onto the one or more optically transparent sample holders.

7. The imaging platform of claim 1, wherein the translation stage further comprises one or more linear motion shafts holding the moveable scanning head and a stepper motor coupled to the moveable scanning head via a belt.

8. The imaging platform of claim 1, wherein the moveable scanning head further comprises a one or more heat sinks for the image sensor(s).

9. The imaging platform of claim 1, wherein the computational motion analysis software performs object function normalization (OFN) to suppress strongly scattering objects within the sample.

10. A method of using the imaging platform of claim 1, comprising:
    loading the sample into the one or more optically transparent sample holders;
    translating the moveable scanning head to different regions of the one or more optically transparent sample holders;
    obtaining time-varying holographic speckle pattern image sequences using the image sensor(s);
    identifying the motile objects in the sample using the computational motion analysis software; and
    classify the motile objects in the sample using the deep learning-based classifier software.

11. The method of claim 10, wherein the sample is first exposed to a lysis buffer prior to loading.

12. The method of claim 10, wherein the sample is allowed to settle prior to translating the moveable scanning head.

13. The method of claim 10, wherein the deep learning-based classifier software outputs a count of motile objects in the sample.

14. The method of claim 10, wherein the deep learning-based classifier software outputs a concentration of motile objects in the sample.

15. The method of claim 10, wherein the deep learning-based classifier software outputs a positive or negative classification for the sample based on a count or concentration of motile objects in the sample.

16. The method of claim 10, wherein the sample is a biological sample.

17. The method of claim 10, wherein the sample is an environmental sample.

18. The method of claim 10, wherein the motile objects comprise parasites.

19. A method of detecting motile objects in a sample comprising:

obtaining a plurality of time-varying holographic speckle pattern image sequences of the sample using a moveable scanning head containing one or more coherent light sources and corresponding image sensor(s) associated with the one or more coherent light sources wherein no lens is present between the one or more coherent light sources and the corresponding image sensor(s); and processing the plurality of time-varying holographic speckle pattern image sequences with a computing device configured to receive the time-varying holographic speckle pattern image sequences obtained by the image sensor(s), the computing device comprising computational motion analysis software configured to generate a three-dimensional (3D) contrast map of the motile objects within the one or more optically transparent sample holders that back-propagates the time-varying holographic speckle pattern image sequences followed by differential analysis, image filtering, and thresholdinq to find connected regions, the computing device further comprising a deep learning-based classifier software to identify motile objects in the three-dimensional (3D) contrast map.

20. The method of claim 19, further comprising the computing device outputting a count of the motile objects.

21. The method of claim 19, further comprising the computing device outputting a concentration of the motile objects in the sample.

* * * * *